United States Patent
Barlaam et al.

(10) Patent No.: US 7,342,020 B2
(45) Date of Patent: *Mar. 11, 2008

(54) ARYLPIPERAZINES AND THEIR USE AS METALLOPROTEINASE INHIBITING AGENTS (MMP)

(75) Inventors: Bernard Christophe Barlaam, Reims (FR); Nicholas John Newcombe, Cheshire (GB); Howard Tucker, Cheshire (GB); David Waterson, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 583 days.

This patent is subject to a terminal disclaimer.

(21) Appl. No.: 10/787,775

(22) Filed: Feb. 26, 2004

(65) Prior Publication Data

US 2004/0171641 A1    Sep. 2, 2004

Related U.S. Application Data

(63) Continuation of application No. 09/763,709, filed as application No. PCT/GB99/02801 on Aug. 25, 1999.

(30) Foreign Application Priority Data

Aug. 31, 1998  (EP) ................... 98402144
Jun. 4, 1919   (EP) ................... 99401351

(51) Int. Cl.
  *C07D 401/04*  (2006.01)
  *C07D 401/06*  (2006.01)
  *C07D 401/14*  (2006.01)
  *A61K 31/4523* (2006.01)

(52) U.S. Cl. .............. 514/256; 546/187; 544/335; 514/318; 514/326

(58) Field of Classification Search ........... 546/187; 544/335; 514/318, 256, 326
See application file for complete search history.

(56) References Cited

U.S. PATENT DOCUMENTS

| | | | |
|---|---|---|---|
| 5,998,412 A | 12/1999 | Broka et al. |
| 6,100,266 A | 8/2000 | Montana et al. |
| 6,130,220 A | 10/2000 | Broka et al. |
| 6,143,744 A | 11/2000 | Broka et al. |
| 6,235,786 B1 | 5/2001 | Dai et al. |
| 6,294,573 B1 | 9/2001 | Curtin et al. |
| 6,376,506 B1 | 4/2002 | Broka et al. |
| 6,479,502 B1 | 11/2002 | Martin |
| 6,482,827 B1 | 11/2002 | Alpegiani |
| 2003/0050310 A1 | 3/2003 | Martin |

FOREIGN PATENT DOCUMENTS

| | | |
|---|---|---|
| DE | 198 02 350 | 7/1998 |
| WO | WO-98/16514 | 4/1998 |
| WO | WO-99/02510 | 1/1999 |
| WO | WO-99/38843 | 8/1999 |

OTHER PUBLICATIONS

Coussens et al. {SCIENCE, vol. 295, Mar. 29, 2002}.*

* cited by examiner

*Primary Examiner*—Kahsay Habte
(74) *Attorney, Agent, or Firm*—Ropes & Gray LLP

(57) ABSTRACT

Arylpiperazines of formula (I) useful as metalloproteinase inhibitors, especially as inhibitors of MMP 13

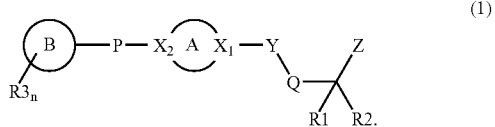

7 Claims, No Drawings

ARYLPIPERAZINES AND THEIR USE AS METALLOPROTEINASE INHIBITING AGENTS (MMP)

RELATED APPLICATIONS

This application is a continuation of U.S. application Ser. No. 09/763,709, filed Feb. 26, 2001, which is a national stage filing under 35 U.S.C. 371 of International Application No. PCT/GB99/02801, filed Aug. 25, 1999, which claims priority from European Application No. 98402144.4, filed Aug. 31, 1998, and European Application No. 99401351.4, filed Jun. 4, 1999, the specifications of each of which are incorporated by reference herein. International Application PCT/GB99/02801 was published under PCT Article 21(2) in English.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1-6. Examples of metalloproteinases include the matrix metalloproteinases (MMP) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265-279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease)); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; and extracellular matrix remodelling observed in cardiovascular diseases such as restenosis and atherosclerosis.

A number of metalloproteinase inhibitors are known; different classes of compounds may have different degrees of potency and selectivity for inhibiting various metalloproteinases. We have discovered a new class of compounds that are inhibitors of metalloproteinases and are of particular interest in inhibiting MMP-13, as well as MMP-9. The compounds of this invention have beneficial potency and/or pharmacokinetic properties.

MMP13, or collagenase 3, was initially cloned from a cDNA library derived from a breast tumour [J. M. P. Freije et al. (1994) Journal of Biological Chemistry 269(24): 16766-16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243-250], squamous cell carcinomas [N. Johansson et al., (1997) Am. J. Pathol. 15I(2):499-508] and epidermal tumours [K. Airola et al., (1997) J. Invest. Dermatol. 109(2):225-231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest. 97(3):761-768; V. Knauper et al., (1996) The Biochemical Journal 271; 1544-1550], MMP13 has been hypothesised to serve a role during primary ossification and skeletal remodelling [M. Stahle-Backdahl et al., (1997) Lab. Invest. 76(5):717-728; N. Johansson et al., (1997) Dev. Dyn. 208(3):387-397], in destructive joint diseases such as rheumatoid and osteo-arthritis [D. Wernicke et al., (1996) J. Rheumatol. 23:590-595; P. G. Mitchell et al., (1996) J. Clin. Invest. 97(3):761-768; O. Lindy et al., (1997) Arthritis Rheum 40(8):1391-1399]; and during the aseptic loosening of hip replacements [S. Imai et al, (1998) J. Bone Joint Surg. Br. 80(4):701-710]. MMP13 has also been implicated in chronic adult periodontitis as it has been localised to the epithelium of chronically inflamed mucosa human gingival tissue [V. J. Uitto et al., (1998) Am. J. Pathol 152(6):1489-1499] and in remodelling of the collagenous matrix in chronic wounds [M. Vaalamo et al., (1997) J. Invest. Dermatol. 109(I):96-101].

MMP9 (Gelatinase B; 92 kDa Type IV Collagenase; 92 kDa Gelatinase) is a secreted protein which was first purified, then cloned and sequenced, in 1989 (S. M. Wilhelm et al (1989) J. Biol Chem. 264 (29): 17213-17221. Published erratum in J. Biol Chem. (1990) 265 (36): 22570.). A recent review of MMP9 provides an excellent source for detailed information and references on this protease : T. H. Vu & Z. Werb (1998) (In: Matrix Metalloproteinases. 1998. Edited by W. C. Parks & R. P. Mecham. pp115-148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, it's expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases -1), a naturally-occurring protein. TIMP-1 binds to the C-terminal region of P9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues. Increased MMP9 expression has observed in certain pathological conditions, therebye implicating MMP9 in disease processed such as arthritis, tumour metastasis, Alzheimer's, Multiple Sclerosis, and plaque rupture in atherosclerosis leading to acute coronary conditions such as Myocardial Infarction.

In a first aspect of the invention we provide compounds of the formula I

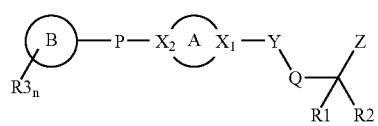

wherein ring B is a monocyclic or bicyclic alkyl, aryl, aralkyl, heteroaryl or heteroaralkyl ring comprising up to 12 ring atoms and containing one or more heteroatoms independently chosen from N, O, and S; alternatively ring B may be biphenyl; ring B may optionally be linked to ring A by a C1-4 alkyl or a C1-4 alkoxy chain linking the 2-position of ring B with a carbon atom alpha to X2;

each R3 is independently selected from hydrogen, halogen, NO2, COOR wherein R is hydrogen or C1-6alkyl, CN, CF3, C1-6 alkyl, —S—C1-6 alkyl, —SO—C1-6 alkyl, —SO2-C1-6 alkyl, C1-6 alkoxy and up to C10 aryloxy, n is 1,2 or 3;

P is —(CH$_2$)n- wherein n=0, 1, 2, or P is an alkene or alkyne chain of up to six carbon atoms; where X2 is C, P may be -Het-, —(CH[R6])n-Het-, -Het-(CH[R6]n-or -Het-(CH[R6])n-Het-, wherein Het is selected from —CO—, —S—, SO—, —SO2—, —NR6—, or —O— wherein n is 1 or 2, or P may be selected from —CO—N(R6)—, —N(R6)—CO—, —SO2N(R6)- and —N(R6)—SO2—, and R6 is hydrogen, C1-6 alkyl up to C10 aralkyl or up to C9 heteroalkyl;

Ring A is a 5-7 membered aliphatic ring and may optionally be mono- or di-substituted by optionally substituted C1-6 alkyl or C1-6 alkoxy, each substituent being independently selected from halogen, C1-6 alkyl or an oxo group;

X1 and X2 are independently selected from N and C, where a ring substituent on ring A is an oxo group this is preferably adjacent a ring nitrogen atom;

Y is selected from —SO2— and —CO—;

Z is —CONHOH, Y is —CO— and Q is selected from —C(R6)(R7)—, —C(R6)(R7)—CH2—, —N(R6)—, and —N(R6)—CH2— wherein R6 is as defined above, and solely in relation to Q as here defined, R6 may also represent up to C10 aryl and up to C9 heteroaryl, and R7 is H, C1-6 alkyl, or together with R6 forms a carbocyclic or heterocyclic spiro 5, 6 or 7 membered ring, the latter containing at least one heteroatom selected from N, O, and S;

Z is —CONHOH, Y is —SO2— and Q is selected from —C(R6)(R7)—, and —C(R6)(R7)—CH2—;

or Z is —N(OH)CHO and Q is selected from —CH(R6)—, —CH(R6)—CH2—, and —N(R6)—CH2—;

R1 is H, C1-6 alkyl, C5-7 cycloalkyl, up to C10aryl, up to C10heteroaryl, up to C12aralkyl, or up to C12 heteroaryla-lkyl, all optionally substituted by up to three groups independently selected from NO2, CF3, halogen, C1-4alkyl, carboxy(C1-4)alkyl, up to C6cycloalkyl, —OR4, —SR4, C1-4alkyl substituted with —OR4, SR4 (and its oxidised analogues), NR4, N—Y—R4, or C1-4alkyl-Y—NR4, with the proviso that where R1 is —OH, —OR4, —SR4, or NR4, or N—Y—R4 then Z is not —N(OH)CHO, or R1 is 2,3,4,5,6-pentafluorophenyl;

R4 is hydrogen, C1-6 alkyl, up to C10 aryl or up to C10 heteroaryl or up to C9 aralkyl, each independently optionally substituted by halogen, NO2, CN, CF3, C1-6 alkyl, —S—C1-6 alkyl, —SO—C1-6 alkyl, —SO2-C1-6 alkyl or C1-6 alkoxy;

R2 is H, C1-6 alkyl, or together with R1 forms a carbocyclic or heterocyclic spiro 5, 6 or 7 membered ring, the latter containing at least one heteroatom selected from N, O, and S;

also the group Q can be linked to either R1 or R2 to form a 5, 6 or 7 membered alkyl or heteroalkyl ring comprising one or more of O, S and N.

Any alkyl groups outlined above may be straight chain or branched.

Convenient values for the above groups include the following:

ring A=a 5-6 membered aliphatic ring, such as a piperazine ring, and may optionally be mono- or di-substituted by optionally substituted C1-6 alkyl or C1-6 alkoxy, each substituent being independently selected from halogen, C1-6 alkyl or an oxo group;

R3=hydrogen, halogen, NO2, CF3, C1-4 alkyl, and C1-4 alkoxy, n is 1 or 2, such as individually 4-fluoro, CF3, 4-chloro and 3,4-dichloro;.

ring B=monocyclic or bicyclic aryl, aralkyl or heteroaryl having up to 10 ring atoms, especially monocyclic aryl, aralkyl or heteroaryl having up to 7 ring atoms, more especially monocyclic aryl or heteroaryl having up to 6 ring atoms, such as a phenyl or pyridyl ring;

P=—(CH2)n— wherein n is 0 or 1, or —O—, or —CO—N(R6)—;

one or both of X2 and X1=N, or X1 is N, or X2 is C;
Y=—SO2—, Y=—CO—;
Q=—CH(R6)—, —CH(R6)—CH2—, and —N(R6)—CH2— wherein R6 is hydrogen or C1-6 alkyl; also where Q is linked to R1 or R2 to form a C5-7 alkyl or heteroalkyl ring such as a cyclohexyl ring;
R1=hydrogen, C1-6alkyl, C5-7 cycloalkyl, up to C12aralkyl, up to C11Heteroarylalkyl, up to C10 aryl or heteroaryl such as up to C6 aryl; all optionally substituted by up to three halogen atoms, or by CF3;
R2=hydrogen, or together with R1 represent a carbocyclic or heterocyclic spiro 5-or 6 membered ring, such as a tetrahydropyran ring;
R4=up to C10 aryl optionally substituted by halogen, NO2, CN, CF3, C1-6 alkyl, —S—C1-6 alkyl, —SO—C1-6 alkyl, —SO2-C1-6 alkyl or C1-6 alkoxy;
Z=—CONHOH—, Z=—N(OH)CHO.

Preferred values for the above groups include the following:
R3=hydrogen, halogen such as chlorine, bromine or fluorine, NO2, CF3, methyl, ethyl, methoxy, ethoxy, particularly methoxy or fluorine;
ring B=a monocyclic aryl, aralkyl or heteroaryl ring having up to 7 ring atoms such as phenyl, biphenyl, napthyl, pyridyl, pyrimidinyl, pyrazinyl and pyridazinyl, especially phenyl, pyridyl and pyrimidyl, more especially phenyl, 2-pyridyl and 2,4-pyrimidyl;
P=a direct bond;
both X2 and X1 are N;
Y=—SO2—;
Q=—CH2—;
R1 is phenyl, 4-trifluoromethylphenyl phenethyl, phenpropyl, isobutyl, cyclopentyl, benzyloxymethyl, 3,4-dichlorophenyl, pyridyl, pyridylethyl, thiophenylpropyl, bromothiophenyl, pyrimidinylethyl, pyrimidinylpropyl, pyridylethyl, pyridylpropyl or together with R2 is spirocyclohexane or spiro-4-pyran; R2 is hydrogen
Z=—N(OH)CHO.
More preferred values include R3 being halogen, the substituent is preferably meta or para to the ring junction where ring B is an aryl or heteroaryl ring, where ring B is phenyl then especially 4-fluoro and where ring B is pyridyl then 3-, or 4-chloro (as appropriate);
Q=—CH2—.
Preferred combinations of Rings B and A include phenyl and piperazinyl; pyridyl and piperazinyl, and pyrimidine and piperazinyl respectively.
Particular alicyclic, fused and heterocyclic rings for ring B include any one of

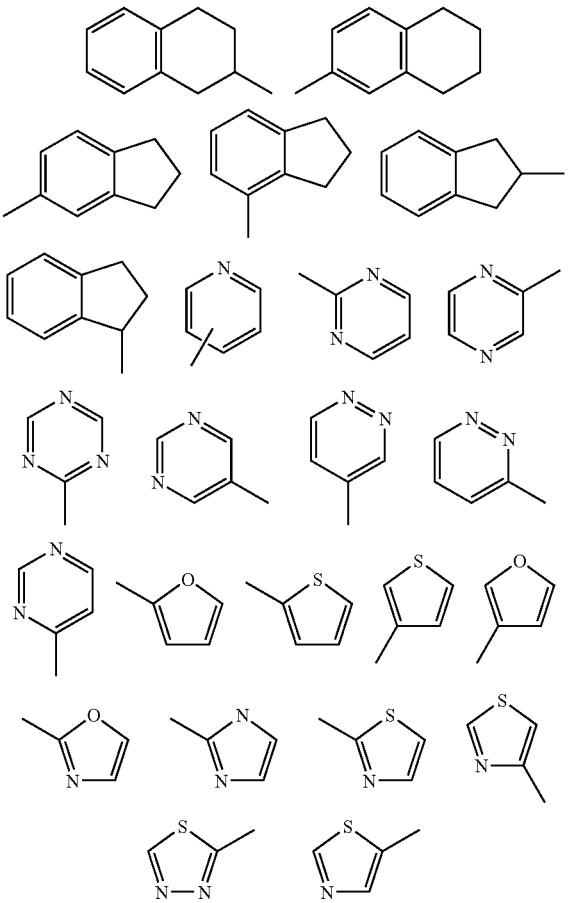

Particular rings for ring A include any one of

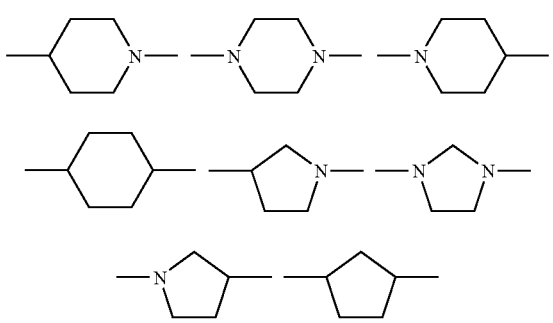

and its corresponding seven membered analogue(s).

It will be appreciated that the particular substitituents and number of substituents on rings A and B are selected so as to avoid sterically undesirable combinations. This also applies to rings as may be formed by R1 and Q, R2 and Q as well as R6 and R7.

Where optically active centres exist in the compounds of formula I, we disclose all individual optically active forms and combinations of these as individual specific embodiments of the invention, as well as their corresponding racemates.

Specific compounds include
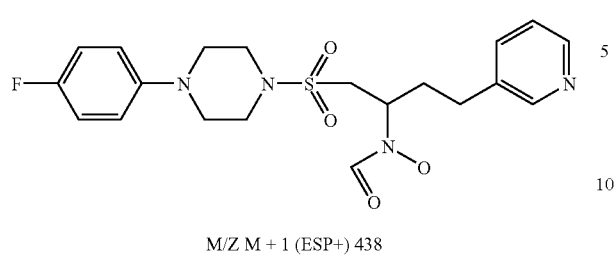
M/Z M + 1 (ESP+) 438
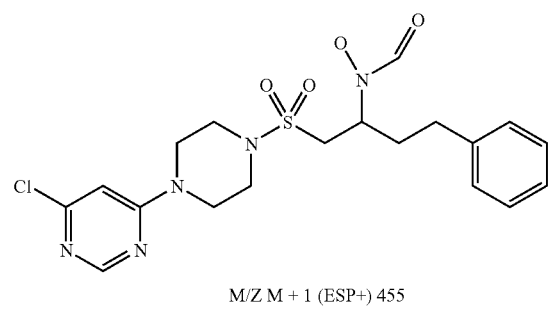
M/Z M + 1 (ESP+) 455
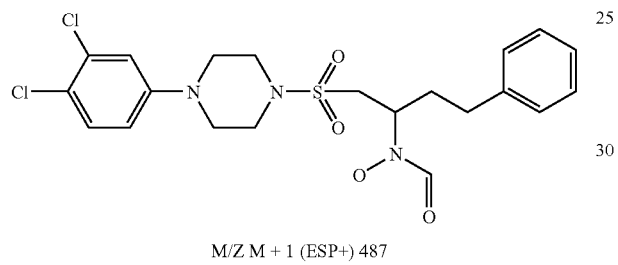
M/Z M + 1 (ESP+) 487
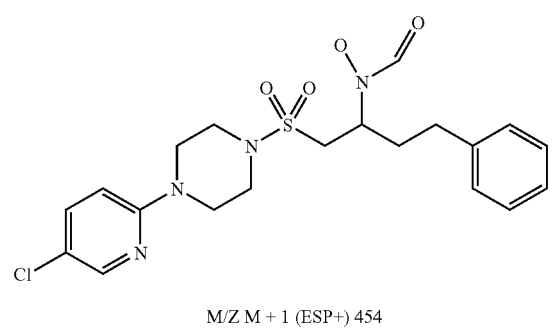
M/Z M + 1 (ESP+) 454
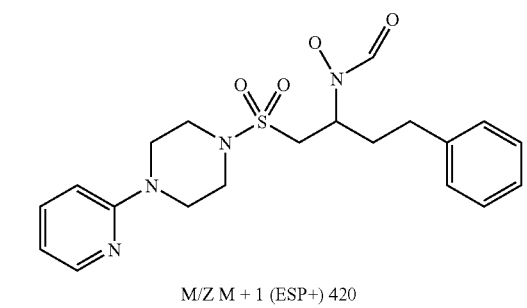
M/Z M + 1 (ESP+) 420
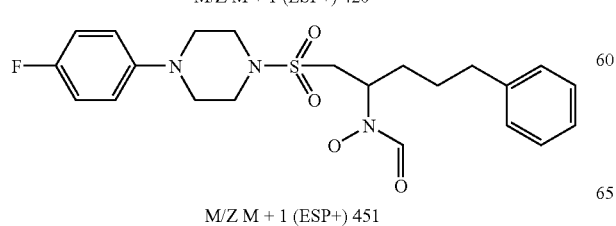
M/Z M + 1 (ESP+) 451
-continued
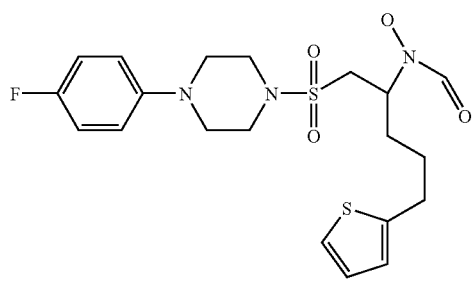
M/Z M + 1 (ESP+) 457
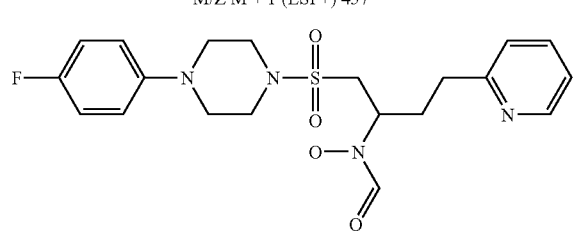
M/Z M + 1 (ESP+) 438
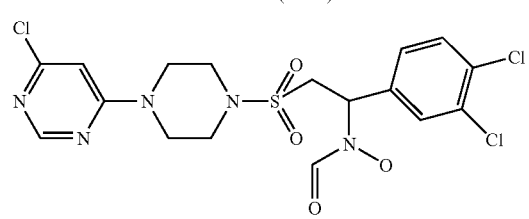
M/Z M + 1 (ESP+) 496
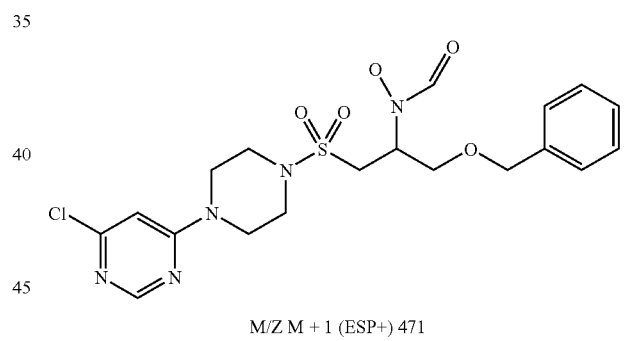
M/Z M + 1 (ESP+) 471
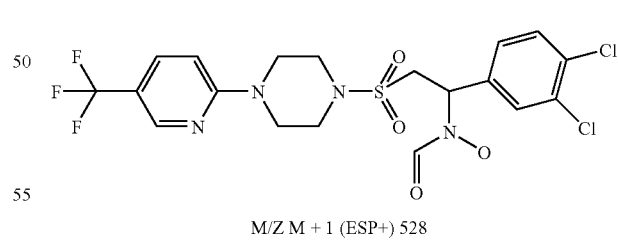
M/Z M + 1 (ESP+) 528
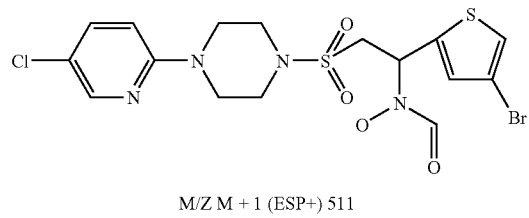
M/Z M + 1 (ESP+) 511

-continued
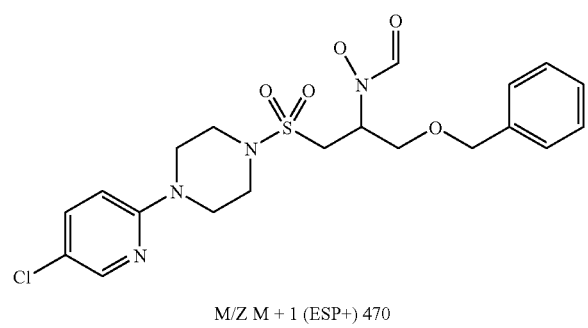
M/Z M + 1 (ESP+) 470
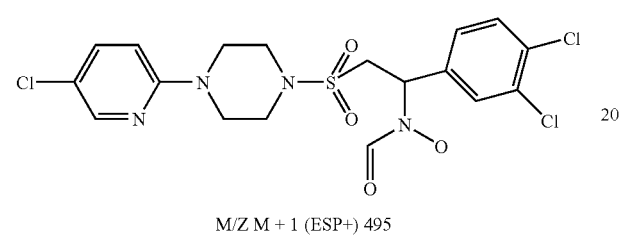
M/Z M + 1 (ESP+) 495
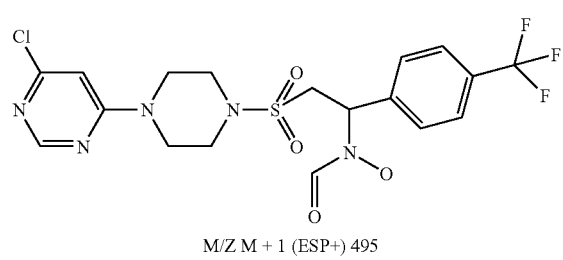
M/Z M + 1 (ESP+) 495
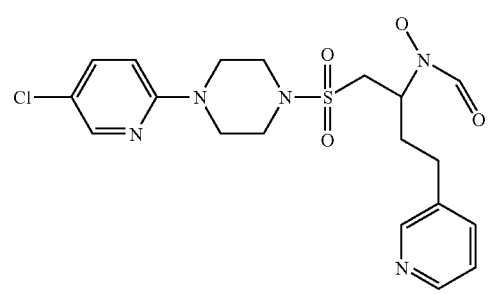
M/Z M + 1 (ESP+) 455
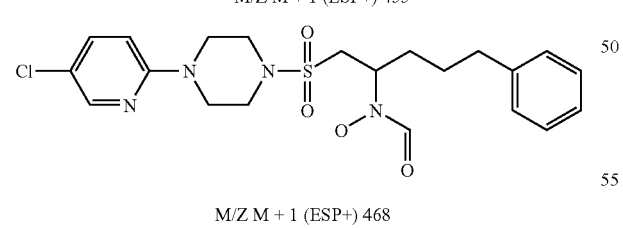
M/Z M + 1 (ESP+) 468
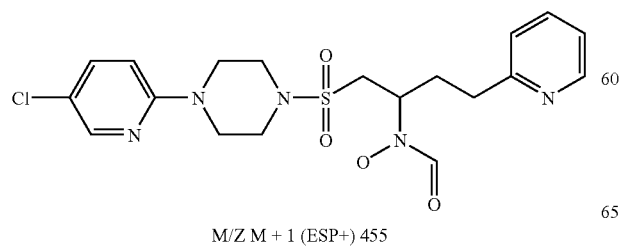
M/Z M + 1 (ESP+) 455
-continued
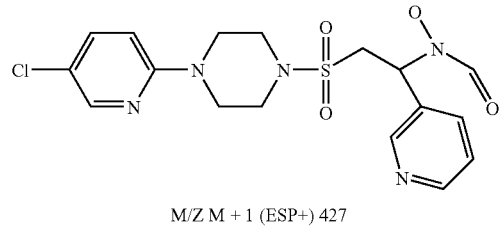
M/Z M + 1 (ESP+) 427
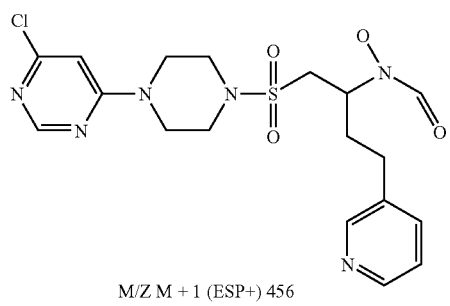
M/Z M + 1 (ESP+) 456
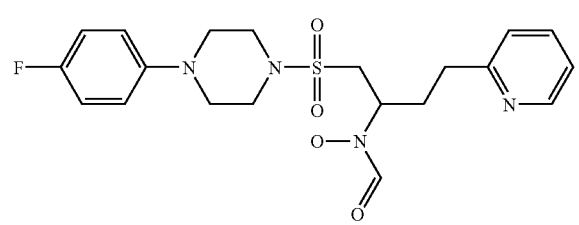
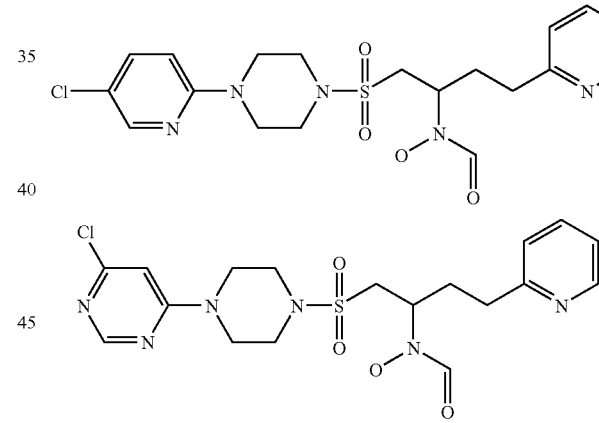
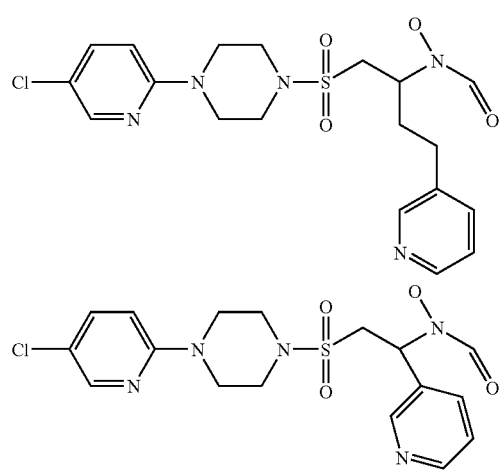

-continued

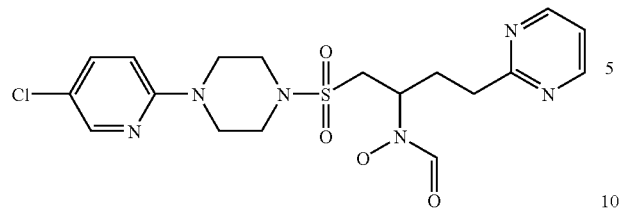

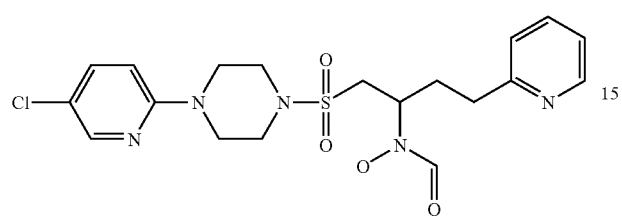

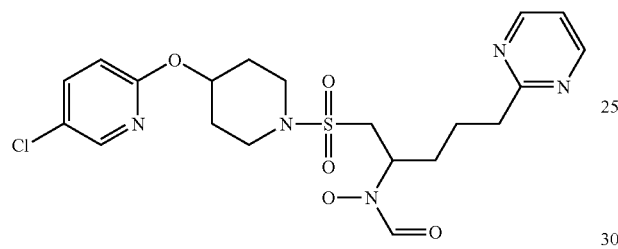

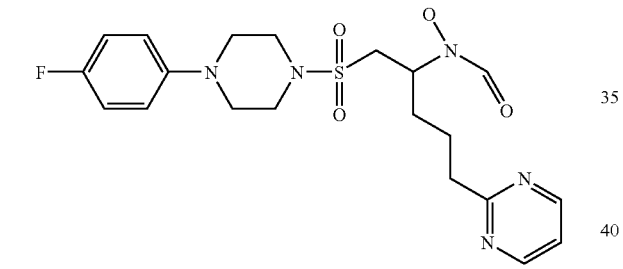

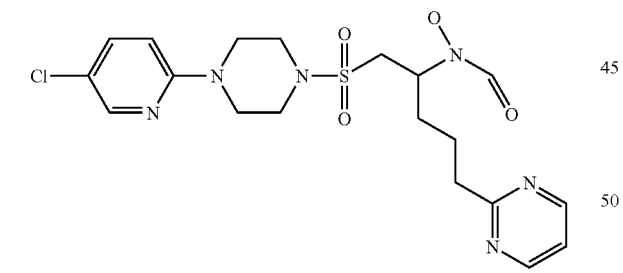

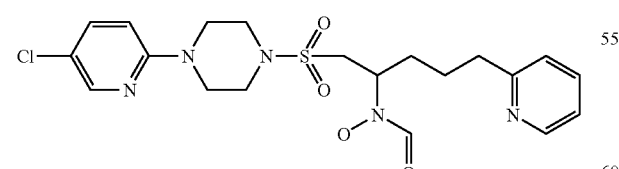

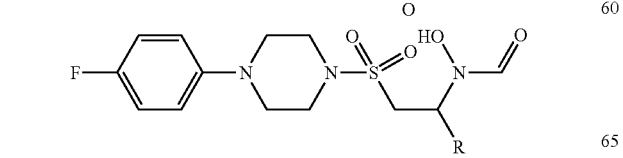

wherein R=phenyl or phenethyl and

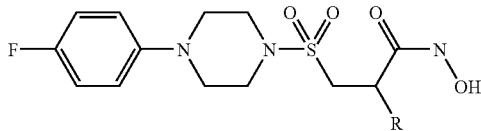

wherein R=isobutyl or a spiro-4-pyran ring

As previously outlined the compounds of the invention are metalloproteinase inhibitors, in particular they are inhibitors of MMP13. Each of the above indications for the compounds of the formula I represents an independent and particular embodiment of the invention. Whilst we do not wish to be bound by theoretical considerations, the compounds of the invention are believed to show selective inhibition for any one of the above indications relative to any MMP1 inhibitory activity, by way of non-limiting example they may show 100-1000 fold selectivity over any MMP1 inhibitory activity.

In addition we have found that compounds of the formula 1 wherein ring B is phenyl, pyridyl (such as 2-pyridyl or 3-pyridyl, especially 2-pyridyl) ring optionally mono- or di-substituted, preferably mono-substituted, by halogen (for example chlorine), P is a direct bond; ring A is a piperazinyl or piperidinyl ring, Y is —SO2- and Q is C1-4alkylene (for example —CH2—), especially —CH2—; R1 is as defined for Formula 1 and is especially 2-phenylpropyl, 2-(2-pyridyl)propyl, 2-(3-pyridyl)propyl, 2-(4-pyridyl)propyl, phenyl, benzyloxymethyl, 4-phenylbutyl, 2-phenylbutyl, or 2-(2-thienyl)propyl; and Z is —N(OH)CHO; are of particular use as aggrecanase inhibitors ie. inhibitors of aggrecan degradation. Of particular note are compounds of the formula I wherein ring B is a phenyl, 3-methylphenyl, 4-fluorophenyl, 3-chlorophenyl, 4-chlorophenyl, or 3,4-dichlorophenyl ring or 5-chloro-2-pyridyl; P is a direct bond; ring A is piperidinyl or piperazinyl especially piperazinyl, Y is SO2, Q is —CH2-, Z is —N(OH)CHO and R1 is phenyl, phenbutylene, phenisopropylene, 2-pyridylethylene, 2-pyridylisopropylene, 3-pyridylisopropylene, 4-pyridylisopropylene, or 4-chlorophenyloxydimethylmethylene. Also of mention are compounds of the formula I wherein ring B is phenyl monosubstituted by chlorine or fluorine, especially 4-chlorophenyl and 4-fluorophenyl; P is a direct bond; ring A is piperidinyl, Y is SO2, Q is —CH2—, Z is —CONHOH and R1 is hydrogen, i-butyl, or spiro-tetrahydropyranyl.

Particular compounds include

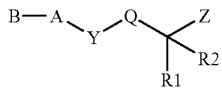

| B | A | Y | Q | R1 | Z |
|---|---|---|---|----|----|
| 4-F-Ph | PIP | SO2 | CH2 | CH2CH(CH3)Ph | RH |
| 4-F-Ph | PIP | SO2 | CH2 | PhCH2CH2CH2CH2 | RH |
| 3-Cl-Ph | PIP | SO2 | CH2 | PhCH2OCH2 | RH |
| 4-F-Ph | PIP | SO2 | CH2 | 4-PyridylCH(CH3)CH2 | RH |
| 4-F-Ph | Piperidinyl | SO2 | CH2 | PhCH(CH3)CH2 | RH |
| 4-F-Ph | PIP | SO2 | CH2 | (R)-2-PhCH(CH3)CH2 | RH |
| 3-Cl-Ph | PIP | SO2 | CH2 | 3-PyridylCH(CH3)CH2 | RH |
| 3-CH3-Ph | PIP | SO2 | CH2 | Ph | RH |
| 4-F-Ph | PIP | SO2 | CH2 | CH2CH(CH2CH3)Ph | RH |
| 5-Cl-2- | PIP | SO2 | CH2 | 3-PyridylCH(CH3)CH2 | RH |

-continued

B—A—Y—Q—Z / R2 / R1

| B | A | Y | Q | R1 | Z |
|---|---|---|---|---|---|
| Pyridyl 4-F-Ph | PIP | SO2 | CH2 | 2-thiophenylCH(CH3)CH2 | RH |
| 4-F-Ph | PIP | SO2 | CH2 | 2-CH3PhCH2CH2 | RH |
| 4-F-Ph | Piperidinyl | SO2 | CH2 | 3-PyridylCH(CH3)CH2 | RH |
| 4-Br-Ph | PIP | SO2 | CH2 | PhCH(CH3)CH2 | RH |
| 4-F-Ph | PIP | SO2 | CH2 | 4-F-PhCH(CH3)CH2 | RH |
| 4-F-Ph | PIP | SO2 | CH2 | 2-PyrazinylCH(CH3)CH2 | RH | wherein
PIP = piperazinyl
RH = reverse hydroxamate group and
R2 = hydrogen

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal the compound under test and subsequently examining the test animal's body fluids. Suitable in vivo hydrolysable esters for carboxy include methoxymethyl and for hydroxy include formyl and acetyl, especially acetyl.

In order to use a compound of the formula (I) or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or in vivo hydrolysable ester thereof for use in a method of therapeutic treatment of the human or animal body.

In yet a further aspect the present invention provides a method of treating a metalloproteinase mediated disease condition which comprises administering to a warm-blooded animal a therapeutically effective amount of a compound of the formula (I) or a pharmaceutically acceptable salt or in vivo hydrolysable ester thereof In another aspect the present invention provides a process for preparing a compound of the formula (I) or a pharmaceutically acceptable salt or in vivo hydrolysable ester thereof which process comprises a) reacting a compound of the formula (II) or a pharmaceutically acceptable salt or in vivo hydrolysable ester thereof with a compound of the formula (III)

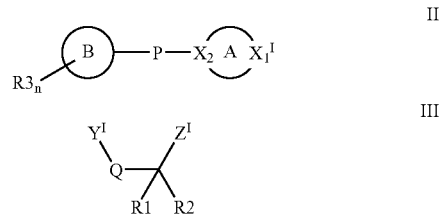

wherein $X_1^I$ represents X or a precursor of X (whether by modification or displacement) or an activated form of X suitable for reaction with $Y_1$;

$Y_1$ represents Y, a precursor of Y, or an activated form of Y suitable for reaction with $X_1^I$; by way of non-limiting example, when X is C then $X_1$ may be derivatised to include a precursor of Y for reaction with a compound of formula III wherein $Y^I$ is a precursor of Y; $Z^I$ represents a protected form of Z, a precursor of Z (whether by modification or displacement of $Z^I$) or an activated form of Z;

and where Q=—(CH$_2$)(R6)— then by reacting a compound of the formula IX with an appropriate compound of the formula R1—CO—R2 to yield an alkene of the formula X which is then converted to a compound of the formula XI wherein Z* is a hydroxylamine precursor of the group Z, and then converting Z* to the group Z, all as set out below:

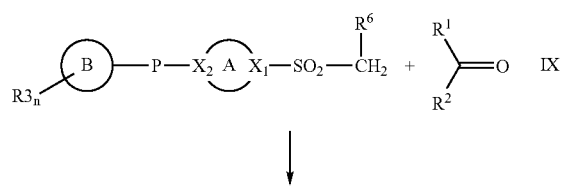

-continued

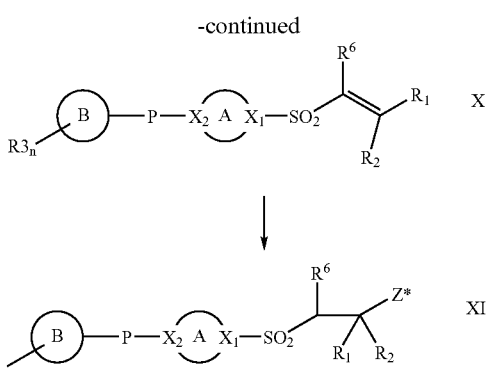

or b) reacting a compound of the formula (IV)) or a pharmaceutically acceptable salt or in vivo hydrolysable ester thereof with a compound of the formula (V).

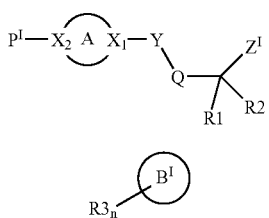

wherein $B^I$ represents a suitable ring function or substituent group for reaction with $P^I$;

$Z^I$ is as hereinbefore defined; and $P^i$ represents a suitably activated form of the linker P for reaction with $B^I$ or where X2=N then P1 may be present on ring A rather than ring B or; as required, the linker P may be formed by appropriate reaction of precursor groups P''' and P'''' provided on rings $B^I$ and A respectively, or vice versa.

A compound of the formula (II) is conveniently prepared by reacting a compound of the formula (VI) with a compound of the formula (VII)

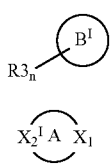

wherein $B^I$ represents a suitable ring function or substituent group, $X_2^I$ represents X or a precursor of X (whether by modification or displacement) or an activated form of X suitable for reaction with $B^I$ and wherein $B^I$ and $X_2^I$ when reacted together provide the linker P between ring A and ring B in the compound of formula (II). By way of non-limiting example, when $X_2$ is N then ring B is suitably derivatised to introduce the linker P via $B^I$, and when $X_2$ is C then both ring B and ring A are suitably derivatised to provide the linker P by the reaction of $B^I$ and $X_2^I$.

It will be appreciated that many of the relevant starting materials are commercially available. In addition the following table shows details of aldehyde intermediates and their corresponding registry numbers in Chemical Abstracts.

| RCHO | Chemical Abstracts Registry Numbers |
| --- | --- |
| 2-methyl-2-(4-chlorophenoxy)propionaldehyde | 6390-87-0 |
| 2-methyl-2(4-chlorophenylthio)-propionaldehyde | 56421-90-0 |
| 4-phenoxybutyraldehyde | 19790-62-6 |
| cyclohexylacetaldehyde | 5664-21-1 |
| 3-cyclohexylpropionaldehyde | 4361-28-8 |
| 4-cyclohexylbutyraldehyde | 1860-41-9 |
| 3-(3-pyridyl)butyraldehyde | 79240-21-4 |
| 3-(2-pyridyl)propionaldehyde | 2057-32-1 |
| 5-phenylvaleraldehyde | 36884-28-3 |
| 6-phenylhexanal | 16387-61-4 |
| 3-phenylvaleraldehyde | 34097-95-5 |
| 3-(2-thienyl)butyraldehyde | 63362-02-7 |
| 3-(2-methylphenyl)propionaldehyde | 19564-40-0 |
| 3-phenyl-4-methylvaleraldehyde | 54784-84-8 |
| 3-(2-pyrazinyl)butyraldehyde | 177615-94-0 |
| furan-2-carboxaldehyde | 221525-60-6 |
| 3-(4-chlorophenyl)propionaldehyde | 75677-02-0 |
| 3-(4-fluorophenyl)propionaldehde | 63416-70-6 |
| 3-(4-pyridyl)propionaldehyde | 120690-80-4 |
| 4-phenylbutraldehyde | 170650-98-3 |
| 2-pyridylcarboxaldehyde | 1121-60-4 |
| 3-(3-pyridyl)propionaldehyde | 1802-16-0 |
| 3-(2-furyl)propionaldehyde | 4543-51-5 |
| 4-(2-pyridyl)butyraldehyde | 90943-32-1 |
| 4-Bromothiophene-2-carboxaldehyde | 18971-75-8 |
| cyclo pentanecarboxaldehyde | 872-53-7 |
| Benzoxazole, 2-(1-piperazinyl)-(9C1) | 111628-39-8 |
| Benzothiazole, 2-(1-piperazinyl)-(9C1) | 55745-83-0 |
| Benzoxazole, 5-chloro-2-(1-piperazinyl)-(9C1) | 140233-44-9 |
| Benzothiazole, 6-chloro-2-(1-piperazinyl)-(9C1) | 153025-29-7 |
| 3-pyridyl-5-bromo-carboxaldehyde | 113118-81-3 |

Aldehydes Without Chemical Abstracts Registry Numbers 3-(2-pyrimidyl) propionaldehyde. To a solution of 2-Bromopyrimidine (7.95 g, 0.05 M) in acetonitrile (150 mL) was added propargylalcohol (4.2 g, 0.075 M), bis-(triphenylphosphine)-palladium(11)chloride (750 mg, 1 mM), copper iodide (100 mg, 0.5 mM) and triethylamine (25 mL, 0.25 M) and the mixture was stirred and heated at 70° C. for 2 hours. An additional amount of propargyl alcohol (2.1 g, 0.038 M), bis-(triphenylphosphine)-palladium(11)chloride (375 mg, 0.5 mil), and copper iodide (50 mg, 0.25 mil) was then added to the reaction mixture which was stirred and heated at 70° C. for an additional 1 hour.

The reaction mixture was evaporated to dryness and the residue which was pre-adsorbed on to silica, chromatographed. Elution with ethyl acetate gave 3-(2-pyrimidyl) prop-2-yn-3-ol as a yellow solid 4.45 g (66%). NMR ($CDCl_3$) 2.9 (1H, t), 4.5 (2H, d), 7.3. (1H, d), 8.8 (2H, t), MS found $MH^+135$ 3-(2-pyrimidyl) prop-2-yn-1-ol (4.45 g; 0.033 M) was dissolved in ethyl acetate (140 mL), 10% Pd/C (890 mg) was added and the mixture stirred under an atmosphere of hydrogen for 6 hours. The reaction mixture was filtered through Celite and the filtrate evaporated to give 3-(2-pyrimidyl) propan-1-ol as a yellow oil, 4.15 g (91%). NMR ($CDCl_3$) 2.1 (2H, m), 3.2 (2H, t), 3.8 (2H, t), 7.2 (1H, t), 8.7 (2H, d) MS found $MH^+139$.

3-(2-pyrimidyl) propan-1-ol was oxidized to give 3-(2-pyrimidyl) propionaldehyde as a yellow oil NMR ($CDCl_3$) 3.0 (2H, t), 3.4 (2H, t), 7.1 (1H, t), 8.7 (2H, d), 9.9 (1H, s) using the Swern oxidation described in this patent.

Using the procedure described above the following aldehydes were prepared 4-(2-pyrimidyl) butyraldehyde by using 3-butyn-1-ol in place of propargylalcohol NMR CDCl$_3$ 9.8(1H, s), 8.6 (2H, m), 7.15 (1H, m), 3.0 (2H, m), 2.5 (2H, m), 2.2 (2H, m).

4-(5-pyrimidyl) butyraldehyde by using 3-butyn-1-ol in place of propargylalcohol and 5-bromopyrimidine in place of 2-bromopyrimidine NMR CDCl$_3$ 9.8 (1H, s), 9.1 (1H, s), 8.6 ( 2h, s), 2.7 (2H, t), 2.55 (2H, t), 2.0(2H, m).

4-(2-pyridyl) butyraldehyde by using 3-butyn-1-ol in place of propargylalcohol and 2-bromopyridine in place of 2-bromopyrimidine NMR CDCl$_3$ 9.8 (1H, s); 8.6 (1H, d), 7.6 (1H, m); 7.1(2H m); 2.8 (2H, t); 2.55 (2H, t), 2.0(2H, m).

The compounds of the invention may be evaluated for example in the following assays:

Isolated Enzyme Assays

Matrix Metalloproteinase family including for example MMP13.

Recombinant human proMMP13 may be expressed and purified as described by Knauper et al. [V. Knauper et al., (1996) The Biochemical Journal 271:1544-1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4-5 hours at 35° C. in assay buffer (0.1M Tris-HCl, pH 7.5 containing 0.1M NaCl, 20 mM CaCl$_2$, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3-diaminopropionyl.Ala.Arg.NH$_2$ in the presence or absence of inhibitors. Activity is determined by measuring the fluorescence at λex 328 nm and λem 393 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3):263-266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218-220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser. Ser.Arg.Cys (4-(3-succinimid-1-yl)-fluorescein)-NH$_2$ in assay buffer (50 mM Tris HCl, pH 7.4 containing 0.1% (w/v) Triton X-100 and 2 mM CaCl$_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. Ser$^1$ and Pro$^2$ were double-coupled. The following side chain protection strategy was employed; Ser$^1$(Bu$^t$), Gln$^5$(Trityl), Arg$^{8,12}$(Pmc or Pbf), Ser$^{9,10,11}$(Trityl), Cys$^{13}$(Trityl). Following assembly, the N-terminal Fmoc-protecting group was removed by treating the Fmoc-peptidyl-resin with in DMF. The aminopeptidyl-resin so obtained was acylated by treatment for 1.5-2 hr at 70° C. with 1.5-2 equivalents of 4',5'-dimethoxyfluorescein-4(5)-carboxylic acid [Khanna & Ullman, (1980) Anal Biochem. 108:156-161] which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214-228, (1999) Journal of Biological Chemistry, 274 (10), 6594-6601 and the antibodies described therein. The potency of compounds to act as inhibitors against collagenases can be determined as described by T. Cawston and A. Barrett (1979) Anal. Biochem. 99:340-345.

Inhibition of Metalloproteinase Activity in Cell/Tissue Based Activity

Test as an Agent to Inhibit Membrane Sheddases such as TNF Convertase

The ability of the compounds of this invention to inhibit the cellular processing of TNFa production may be assessed in THP-1 cells using an ELISA to detect released TNF essentially as described K. M. Mohler et al., (1994) Nature 370:218-220. In a similar fashion the processing or shedding of other membrane molecules such as those described in N. M. Hooper et al., (1997) Biochem. J. 321:265-279 may be tested using appropriate cell lines and with suitable antibodies to detect the shed-protein.

Test as an Agent to Inhibit Cell Based Invasion

The ability of the compound of this invention to inhibit the migration of cells in an invasion assay may be determined as described in A. Albini et al., (1987) Cancer Research 47:3239-3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640+bicarbonate, penicillin, streptomycin and glutamine) and incubated (160 μl) with 20 μl of test compound (triplicates), in DMSO or appropriate vehicle, for 30 min at 37° C. in a humidified (5% CO$_2$/95% air) incubator, prior to addition of 20 μl LPS (E. coli. 0111:B4; final concentration 10 μg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50-100 μl) and stored in 96 well plates at −70° C. before subsequent analysis for TNFα concentration by ELISA.

Test as in Agent to Inhibit in Vitro Cartilage Degradation

The ability of the compounds of this invention to inhibit the degradation of the aggrecan or collagen components of cartilage can be assessed essentially as described by K. M. Bottomley et al., (1997) Biochem J. 323:483-488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male Wistar Alderley Park (AP) rats (180-210 g) are dosed with compound (6 rats) or drug vehicle (10 rats) by the appropriate route e.g. peroral (p.o.), intraperitoneal(i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 μl of each sample are added to a set format pattern in a 96U well plate. Fifty μl of heparinized human blood is then added to each well, mixed and the plate is incubated for 30 min at 37° C. (humidified incubator). LPS (25 μl; final concentration 10 μg/ml) is added to the wells and incubation continued for a further 5.5 hours. Control wells are incubated with 25 μl of medium alone. Plates are then centrifuged for 10 min at 2000 rpm and 200 μl of the supernatants are transferred to a 96 well plate and frozen at −20° C. for subsequent analysis of TNF concentration by ELISA.

Data analysis by dedicated software calculates for each compound/dose:

$$\text{Percent inhibition of TNF}\alpha = \frac{\text{Mean TNF}\alpha(\text{Controls}) - \text{Mean TNF}\alpha(\text{Treated}) \times 100}{\text{Mean TNF}\alpha(\text{Controls})}$$

Test as an Anti-arthritic Agent

Activity of a compound as an anti-arthritic is tested in the collagen-induced arthritis (CIA) as defined by D. E. Trentham et al., (1977) J. Exp. Med. 146,:857. In this model acid soluble native type II collagen causes polyarthritis in rats when administered in Freunds incomplete adjuvant. Similar conditions can be used to induce arthritis in mice and primates.

Test as an Anti-cancer Agent

Activity of a compound as an anti-cancer agent may be assessed essentially as described in I. J. Fidler (1978) Methods in Cancer Research 15:399-439, using for example the B16 cell line (described in B. Hibner et al., Abstract 283 p75 10th NCI-EORTC Symposium, Amsterdam Jun. 16-19 1998).

The invention will now be illustrated but not limited by the following Examples:

EXAMPLES

Example 1

1-[2-(N-formyl-N-hydroxyamino)-2-phenylethanesulfonyl]-4-(4-fluorophenyl)piperazine

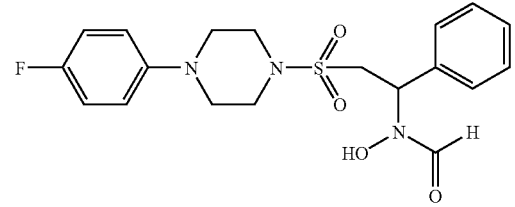

To a solution of 1-[2-(hydroxyamino)-2-phenylethanesulfonyl]-4-(4-fluorophenyl)piperazine (338 mg, 0.89 mmol) in THF (5 ml) and formic acid (2 ml) was added a preformed mixture of formic acid (2 ml) and acetic anhydride (0.5 ml). The mixture was stirred at room temperature for one hour. The mixture was evaporated in vacuo and toluene (2×5 ml) was added and evaporated in vacuo. The residue was taken in $CH_2Cl_2$-methanol (6 ml, 9:1) and silica (1 g) was added. The mixture was stirred for 18 hours. The silica was filtered off and rinsed with $CH_2Cl_2$-methanol (9:1). The residue was purified on silica gel (eluant: $CH_2Cl_2$-MeOH 4%) to give the title compound as a light orange solid (220 mg, 61%).

$^1$H NMR (CDCl$_3$): 8.45 and 8.15 (s, 1H), 7.39 (m, 5H), 6.97 (m, 2H), 6.88 (m, 2H), 5.89 and 5.35 (m, 1H), 4.05 and 3.85 (m, 1H), 3.30-3.53 (m, 5H), 3.20-3.10 (m, 4H); MS (ESI): 408 (MH$^+$), 430 (MNa$^+$); EA: calculated for $C_{19}H_{22}FN_3O_4S$: C 56.01, H 5.44, N 10.31, S 7.87, Found: C 56.01, H 5.52, N 10.04, S 7.39.

The starting material was prepared as follows:

i) To a solution of 1-(4-fluorophenyl)piperazine (35 g, 194 mmol) and pyridine (17.5 ml) in dry dichloromethane (200 ml) at 0° C. was added methanesulfonyl chloride (20 ml, 258 mmol) dropwise. The mixture was stirred for 3 hours at room temperature. The mixture was washed with water and extracted with dichloromethane (2×100 ml). The organic layers were dried with MgSO$_4$ and evaporated in vacuo. The residue was triturated and washed with methanol to give 1-(4-fluorophenyl)-4-(methanesulfonyl)piperazine (39.35 g) as white crystals.

¹H NMR (CDCl₃): 7.00 (m, 2H), 6.90 (m, 2H), 3.40 (m, 4H), 3.20 (m, 4H), 2.83 (s, 3H).

ii) To a solution of LDA [8.5 mmol; prepared by slow addition of n-butyl lithium (3.5 ml, 8.5 mmol, 2.5 M in hexane) to a solution of diisopropylamine (860 mg, 8.5 mmol) in dry THF (5 ml) at −78° C.] at −78° C. was added a solution of 1-(4-fluorophenyl)-4-(methanesulfonyl)piperazine (1 g, 3.87 mmol) in THF (25 ml) dropwise. The mixture was stirred at −78° C. for 1 hour and a solution of diethylchlorophosphate (670 mg; 3.87 mmol) in THF (3 ml) was added. The mixture was stirred at −78° C. for 1 hour and benzaldehyde (450 mg; 4.24 mmol) in THF (3 ml) was added. The mixture was gently warmed to room temperature and stirred for 18 hours. The mixture was washed with aqueous ammonium chloride and extracted with ethyl acetate. The organic layers were washed with water, brine and dried over MgSO₄. Purification of the residue on silica (eluant: dichloromethane) afforded 1-(4-fluorophenyl)-4-(trans-β-styrenesulfonyl)piperazine as a white powder (621 mg, 46%).

¹H NMR (CDCl₃): 7.50 (m, 3H), 7.43 (m, 3H), 6.97 (m, 2H), 6.89 (m, 2H), 6.71 (d, 1H, J=15.4 Hz), 3.37 (m, 4H), 3.19 (m, 4H).

iii) To a solution of 1-(4-fluorophenyl)-4-(trans-β-styrenesulfonyl)piperazine (620 mg, 1.79 mmol) in THF (20 ml) was added hydroxylamine (3 ml, 50% aqueous solution). The mixture was stirred for 18 hours. The solvent was evaporated. The residue was dissolved in dichloromethane and washed with water. The organic layer was dried on MgSO₄ to give 1-[2-(hydroxyamino)-2-phenylethanesulfonyl]-4-(4-fluorophenyl)piperazine (730 mg).

¹H NMR (CDCl₃): 7.4-7.1 (m, 5H), 6.97 (m, 2H), 6.87 (m, 2H), 5.95 (s br, 1H), 4.74 (s, 1H), 4.60 (dd, 1H, J=4 Hz, J'=8.8 Hz), 3.56 (dd, 1H, J=8.8 Hz, J'=14.3 Hz), 3.40 (m, 4H), 3.19 (dd, 1H, J=4 Hz, J'=14.3 Hz), 3.12 (m, 4H).

Example 2

Similarly the following compounds were obtained:

| Compound | Data |
|---|---|
| (structure) | MS (ESI): 436 (MH⁺), 458 (MNa⁺) |
| (structure) | MS (ESI): 400 (MH⁺), 422 (MNa⁺) |
| (structure) | MS (ESI): 476 (MH⁺, ³⁵Cl); 498 (MNa⁺, ³⁵Cl) |
| (structure) | MS (ESI): 422 (MNa⁺) |

Example 3

N-hydroxy-3-[4-(4-fluorophenyl)piperazine-1-sulfonyl]propionamide

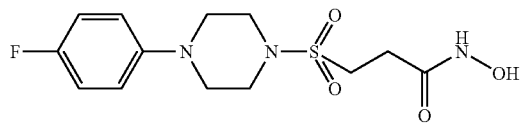

To a solution of N-(2,4-dimethoxybenzyloxy)-N-(2,4,6-trimethoxybenzyl)-3-[4-(4-fluorophenyl)piperazine-1-sulfonyl]propionamide (125 mg, 0.19 mmol) in dichloromethane (2 ml) was added triethylsilane (66 μl, 0.42 mmol) and trifluoroacetic acid (150 μl). The mixture was stirred at room temperature for 4 hours. The solvents were evaporated in vacuo. The residue was purified by chromatography on silica (eluant:dichloromethane, then ethyl acetate then dichloromethane –10% MeOH) to give 35 mg of the title compound.

$^1$H NMR (DMSO d-6+CF$_3$COOD): 7.16 (m, 4H), 3.36 (m, 6H), 3.25 (m, 4H), 2.45 (t, 2H, J=7.4 Hz); MS (ESI): 332 (MN$^+$), 354 (MNa$^+$).

The starting material was obtained as follows:

i) A solution of 3-mercaptopropionic acid (20 g, 185 mmol) in acetic acid (150 ml)-water (30 ml) at 0° C. was reacted with gaseous chlorine (preferably condensed at –78° C., 20 ml). After chlorine had distilled, the solvents were evaporated in vacuo; toluene was added and evaporated to give 1,2-oxathiolane-5-one 2-dioxide (36.12 g).

$^1$H NMR (DMSO d-6): 2.70 (t, 2H, J=7.2 Hz), 2.50 (t, 2H, J=7.2 Hz).

ii) A solution of 1,2-oxathiolane-5-one 2-dioxide (3.8 g, 28 mmol) in thionyl chloride (20 ml) and DMF (5 drops) was stirred at room temperature for 18 hours. The mixture was heated at 40° C. for 1 hour. The solvents were evaporated; toluene was added and evaporated in vacuo to give crude 3-chlorosulfonylpropionyl chloride (NMR purity: 70%, 3.58 g).

$^1$H NMR (CDCl$_3$): 4.02 (t, 2H, J=7.2 Hz), 3.63 (t, 2H, J=7.2 Hz)

iii) To a solution of 3-chlorosulfonylpropionyl chloride (500 mg, 1.83 mmol, 70% purity) and diisopropylethylamine (75 μl) in dichloromethane (5 ml) at –78° C. was added a solution of O-dimethoxybenzyl-N-trimethoxybenzylhydroxylamine[Ref1] (664 mg, 1.83 mmol) and diisopropylethylamine (320 μl, 1.83 mmol) in dichloromethane (5 ml) dropwise over 2 hours. After 30 minutes, a solution of 1-(4-fluorophenyl)piperazine (330 mg, 1.83 mmol) and diisopropylethylamine (320 μl , 1.83 mmol) in dichloromethane (5 ml) was added to the reaction mixture. The solution was warmed to room temperature and stirred for 2 hours. The solution was partitioned between dichloromethane and 1N hydrochloric acid. The organic layers were washed with brine and dried over MgSO$_4$. Chromatography of the residue on silica gel (eluant:ethyl acetate—petroleum ether:gradient from 50/50 to 80/20) gave N-(2,4-dimethoxybenzyloxy)-N-(2,4,6-trimethoxybenzyl)-3-[4-(4-fluorophenyl)piperazine-1-sulfonyl]propionamide (260 mg).

MS (EI): 661 (M$^+$)

Example 4

N-hydroxy-3-[4-benzylpiperazine-1-sulfonyl]propionamide

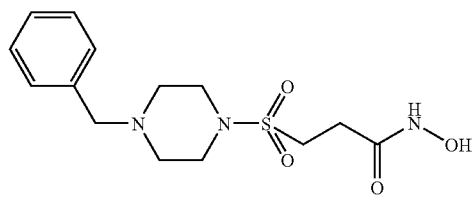

In a manner analogous to that described in Example 3, from 4-benzylpiperazine and 3-chlorosulfonylpropionyl chloride there was obtained the title compound.

$^1$H NMR (DMSO d-6+CF$_3$COOD): 7.50 (m, 5H), 4.41 (s, 2H), 3.78 (m, 2H), 3.41 (m, 4H), 3.18 (m, 2H), 2.43 (t, 2H, J=7.1 Hz); MS (ESI): 328 (MH$^+$).

Example 5

N-hydroxy-3-[4-(4-fluorophenyl)piperazine-1-sulfonyl]-2-isobutylpropionamide

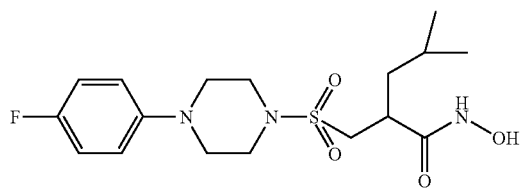

To a solution of N-(2,4-dimethoxybenzyloxy)-3-[4-(4-fluorophenyl)piperazine-1-sulfonyl]-2-isobutylpropionamide (220 mg) in dichloromethane (4 ml) was added trifluoroacetic acid (200 μl) and triethylsilane (145 μl). The mixture was stirred at room temperature for 15 minutes, evaporated in vacuo and the residue was purified on silica gel (eluant:dichloromethane-ether-methanol (8.0:20:0.5) to dichloromethane-methanol (80:20) to give the title compound (88 mg, 56%).

$^1$H NMR (DMSO d-6): 10.72 (s, 1H), 7.08 (m, 2H), 6.99 (m, 2H), 3.37 (dd, 1H, J=8.4 Hz, J'=14.3 Hz), 3.27 (m, 4H), 3.15 (m, 4H), 3.00 (dd, 1H, J=4 Hz, J'=14.3 Hz), 2.62 (m, 1H), 1.6-1.2 (m, 3H), 0.89 (d, 3H, J=6.6 Hz), 0.85 (d, 3H, J=6.6 Hz); MS (ESI): 388 (MH$^+$), 410 (MNa$^+$).

The starting material was obtained as follows:

i) A solution of 3-acetylthio-2-isobutylpropionic acid [obtained by Michael addition of thiolacetic acid onto 2-isobutylacrylic acid] (7 g, 34.3 mmol), benzyl bromide (4.29 ml, 36 mmol) and DBU (5.2 ml, 35 mmol) in toluene (55 ml) was stirred for 18 hours at room temperature. The solvents were evaporated in vacuo. The residue was partitioned between ethyl acetate and 5% sodium bicarbonate. The organic layer was washed with brine and dried over MgSO$_4$. Purification of the residue by chromatography on silica gel (eluant: dichloromethane-ether (9:1)) gave benzyl 3-acetylthio-2-isobutylpropionate (8.4 g)

MS (ESI): 317 (MNa$^+$).

ii) A solution of benzyl 3-acetylthio-2-isobutylpropionate (588 mg, 2 mmol) in acetic acid (12 ml)-water (1.6 ml) at 0° C. was reacted with gaseous chloride (prealably condensed at –78° C., 1.9 ml). After chlorine had distilled, the solvents are evaporated in vacuo to give crude benzyl 3-chlorosulfonyl-2-isobutylpropionate (630 mg).

MS (EI): 318 (N$^+$).

iii) A solution of benzyl 3-chlorosulfonyl-2-isobutylpropionate (630 mg, 2 mmol), 1-(4-fluorobenzyl)piperazine (378 mg, 2.1 mmol) and triethylamine (340 μl, 2.4 mmol) in dichloromethane (15 ml) was stirred at 0° C. for 18 hours. After evaporation of the solvents, the residue was partitioned between ethyl acetate and water. The organic layer was washed with brine and dried over MgSO$_4$. After evaporation of the solvent in vacuo, the residue was purified by chromatography on silica gel (eluant:dichloromethane— ether (9:1) to give benzyl 3-[4-(4-fluorophenyl)piperazine-1-sulfonyl]-2-isobutylpropionate (640 mg)

MS (EI): 462 (M+).

iv) A solution of benzyl 3-[4-(4-fluorophenyl)piperazine-1-sulfonyl]-2-isobutylpropionate (630 mg) in methanol (10 ml) was hydrogenated under 40 PSI pressure for 18 hours in the presence of palladium on charcoal (63 mg, 10%). The catalyst was removed by filtration and the solvents were removed in vacuo to give 3-[4(4-fluorophenyl)piperazine-1-sulfonyl]-2-isobutylpropionic acid (460 mg).

MS (ESI): 373 (MH+), 395 (MNa+).

v) To a solution of 3-[4-(4-fluorophenyl)piperazine-1-sulfonyl]-2-isobutylpropionic acid (230 mg, 0.62 mmol), 2,4-dimethoxybenzylhydroxylamine[ref1] (124 mg, 0.68 mmol), DMAP (75 mg, 0.62 mmol) in DMF (1 ml) was added N-ethyl-N'-(3-dimethylaminopropyl)-carbodiimide hydrochloride (152 mg, 0.8 mmol). The mixture was, stirred at room temperature for 2 days. The reaction mixture was poured in water and extracted with ethyl acetate. The organic layer was washed with 5% sodium bicarbonate, brine and dried over MgSO$_4$. Purification of the residue on silica gel (eluant: dichloromethane—ether: gradient from 9/1 to 8/2) gave N-(2,4-dimethoxybenzyloxy)-3-[4-(4-fluorophenyl)piperazine-1-sulfonyl]-2-isobutylpropionamide (158 mg).

$^1$H NMR (CDCl$_3$): 8.21 (s, 1H), 7.30 (m, 1H), 6.97 (m, 2H), 6.88 (m, 2H), 6.46 (m; 2H), 4.95 (m, 2H), 3.82 (s, 6H), 3.50 (dd, 1H, J=9 Hz, J'=14.2 Hz), 3.37 (m, 4H), 3.14 (m, 4H), 2.84 (dd, 1H, J=14.2 Hz, J'=2 Hz), 2.60 (m, 1H), 1.7-1.2 (m, 3H), 0.90 (m, 6H).

Example 6

4-[4-(4-fluorophenyl)piperazine-1-sulfonylmethyl]tetrahydropyran-4-(N-hydroxy carboxamide)

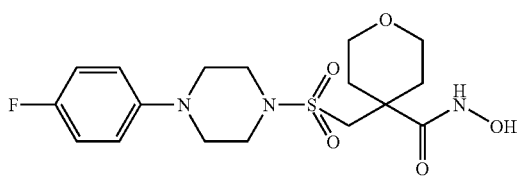

To a solution of 4-[4-(4-fluorophenyl)piperazine-1-sulfonylmethyl]tetrahydropyran-4-carboxylic acid (470 mg, 1.21 mmol) in dichloromethane (8 ml) was added oxalyl chloride (700 mg, 5.6 mmol) and DMF (18 µl). The mixture was heated at 35° C. for 1 hour. After evaporation of the solvents, the crude acid chloride dissolved in dichloromethane (4 ml) was added to a ice-cooled solution of hydroxylamine (440 µl, 50% aqueous solution) in THF (8 ml). The mixture was stirred for 90 minutes at room temperature. After evaporation of the solvents, the residue was triturated in dichloromethane-ether-methanol (80:20:5). The resulting solid was washed with water and .ethyl acetate and dried to give the title compound as white crystals (230 mg, 47%).

hu 1H NMR (DMSO d-6): 10.56 (s br, 1H), 8.74 (s br, 1H), 7.07 (m, 2H), 6.99 (m, 2H), 3.66 (m, 2H), 3.47 (m, 2H), 3.40 (s, 2H), 3.25 (m, 4H), 3.16 (m, 4H), 1.99 (m, 2H), 1.72 (m, 2H); MS (ESI): 402 (MH+), 424 (MNa+).

The starting material was prepared as follows:

(i) Thiolacetic acid (760 µl, 10 mml) and tributylphosphine (2.5 ml, 10 mmol) in DMF (5 ml) was added dropwise to a ice-cooled suspension of sodium hydride (530 mg, 60% in oil, 13 mmol) in DMF (1.5 ml) under an argon atmosphere. The mixture was stirred at 0° C. for 30 minutes. To the above solution was added 2,7-dioxaspiro[3,5]nonane-1-one[Ref2] (1.4 g, 10 mmol) in DMF (10 ml). The mixture was stirred at 0° C. for 30 minutes and at room temperature for 18 hours. The reaction mixture was diluted with ether. The precipitate was filtered and dried to give 4-(acetylthiomethyl)tetrahydropyran-4-carboxylic acid sodium salt.

$^1$H NMR (DMSO d-6): 3.65-3.40 (m, 4H), 2.99 (s, 2H), 2.27 (s, 3H), 1.86 (m, 2H), 1.23 (m, 2H).

(ii) Using the same procedure described in Example 5 i), ii), iii), iv), v) except that no DBU was used in step 1, from 4-(acetylthiomethyl)tetrahydropyran-4-carboxylic acid sodium salt was obtained 4-[4-(4-fluorophenyl)piperazine-1-sulfonylmethyl]tetrahydropyran-4-carboxylic acid (490 mg).

4-(acetylthiomethyl)tetrahydropyran-4-(carboxylic acid benzyl ester): MS (ESI): 331 (MNa+); 4-(chlorosulfonylmethyl)tetrahydropyran-4-(carboxylic acid benzyl ester): MS (ESI): 354 (MNa+); 4-[4-(4-fluorophenyl)piperazine-1-sulfonylmethyl]tetrahydropyran-4-carboxylic acid benzyl ester: MS (ESI): 477 (MH+), 499 (MNa+); 4-[4-(4-fluorophenyl)piperazine-1-sulfonylmethyl]tetrahydropyran-4-carboxylic acid: MS (ESI): 387 (MH+), 409 (MNa+).

Ref 1: B. Barlaam, A. Hamon, M. Maudet; Tetrahedron Lett, 1998,39,7865

Ref 2: F. Hoffmann-La Roche, Agouron Pharm.; Eur. Patent Appl. EP 780386.

Example 7

1-[2-(N-formyl-N-hydroxyamino)-2-phenylethanesulfonyl]-4-phenylpiperazine

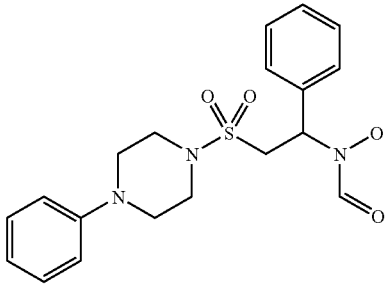

To a solution of 1-[2-(hydroxyamino)-2-phenylethanesulfonyl]-phenylpiperazine (140 mg) in THF (0.75 ml) and formic acid (0.25 ml) was added a preformed mixture of formic acid (0.58 ml) and acetic anhydride (0.29 ml). The solution was stirred at ambient temperature for 18 hours. The mixture was evaporated in vacuo, diluted with dichloromethane and washed with saturated aqueous sodium bicarbonate solution, dried (Na$_2$SO$_4$) and evaporated. The residue was purified by chromatography eluting with 1% methanol in dichloromethane to give 1-phenyl-(4-trans-b-styrenesulfonyl)piperazine (420 mg) as a foam (105 mg).

$^1$H NMR (d6-DMSO at 373K): 9.60 (s, 1H), 8.25 (s, 1H), 7.40 (m, 2H), 7.30 (m, 3H), 7.20 (m, 2H), 6.90 (d, 2H), 6.75 (m, 1H), 5.60 (m, 1H), 3.85 (dd, 1H), 3.60 (dd, 1H), 3.30 (m, 4H); 3.15 (m, 4H) m/z: 390 (M+1).

The starting material was prepared as follows:

A solution of phenylpiperazine (487 mg) in dichloromethane (6 ml) containing triethylamine (0.63 ml) was added dropwise over 5 minutes to trans-b-styrenesulfonyl chloride (638 mg) in dichloromethane (4 ml). The solution was stirred at ambient temperature for 18 hours. The solution was diluted with dichloromethane and washed with water, dried (Na$_2$SO$_4$) and evaporated. The residue was purified by chromatography eluting with 1% methanol in dichloromethane to give 1-phenyl-(4- trans-b-styrenesulfonyl)piperazine (420 mg) as a solid.

$^1$H NMR (d6-DMSO): 7.75 (m, 2H), 7.40 (m, 4H), 7.30 (d, 1H), 7.20 (dd, 2H), 6.90 (d, 2H), 6.80 (dd, 1H), 3.20 (s, 8H) m/z 329 (M+1).

To a solution of 1-phenyl-4-(trans-b-styrenesulfonyl)piperazine (108 mg) in THF (3 ml) was added hydroxylamine (0.45 ml, 50% aqueous solution). The mixture was stirred at ambient temperature for 18 hours. Solvent was removed in vauo and the residue dissolved in dichloromethane, washed with water, dried (Na$_2$SO$_4$) and evaporated to give the product 1-[2-(hydroxyamino)-2-phenylethanesulfonyl]-4-phenylpiperazine as a foam (120 mg).

$^1$H NMR (d6-DMSO): 7.50 (m, 1H), 7.40 (m, 2H), 7.30 (m, 5H), 6.90 (d, 2H), 6.80 (dd, 1H), 5.90 (m, 1H), 4.20 (m, 1H), 3.60 (dd, 1H), 3.40 (dd, 1H), 3.20 (m, 4H); 3.10 (m, 4H) m/z 362 (M+1).

Example 8

1-[2-(N-formyl-N-hydroxyamino)-2-(quinoline-4-yl)ethane-1-sulfonyl]-4-(4-fluorophenyl)piperazine

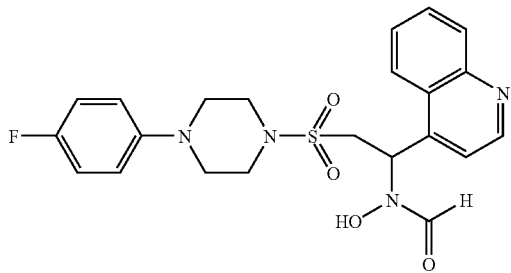

To a suspension of 1-[2-(N-hydroxyamino)-2-(quinoline-4-yl)ethane-1-sulfonyl]-4-(4-fluorophenyl)piperazine (148 mg, 0.34 mmol) in THF (2 ml)—CH$_2$Cl$_2$ (2 ml) was added 5-methyl-3-formyl-1,3,4-thiadiazole-2(3H)-thione[1] (140 mg, 0.87 mmol). The mixture was stirred for 3 h. After addition of methanol (2 ml) and silica (1 g), the mixture was stirred for 18 h. The solids were filtered. The filtrates were washed with sat. NaHCO$_3$ and brine. Evaporation of the solvents followed by trituration in acetonitrile—CH$_2$Cl$_2$ gave the starting material (60 mg). Chromatography of the mother liquors with acetonitrile—CH$_2$Cl$_2$ (1:1) gave the title compound (20 mg, 13%).

$^1$H-NMR (CDCl$_3$): 8.97 (m, 1H), 8.21 (m, 2H), 8.01 (s, 1H), 7.8-7.65 (m, 3H), 6.97 (m, 2H), 6.86 (m, 2H), 5.66 (m, 1H), 3.55-3.1 (m, 10H); MS (ESI): 459 (MH$^+$).

The starting material was prepared from quinoline-4-carboxaldehyde and 1-(fluorophenyl)-4-(methanesulfonyl)piperazine in a similar manner to Example 1 ii-iii): 188 mg: MS (ESI): 431 (MH$^+$); HPLC t$_R$ (Column TSKgel super ODS 2 mm 4.6 mm×5 cm, gradient methanol/water 20 to 100% in 5 min, flow rate: 1.4 ml/mn): 3.43 min (1) Yazawa, H.; Goto, S. Tetrahedron Lett., 1985, 26, 3703

Example 9

1-[1-(N-formyl-N-hydroxyamino)-1-(3,4-dichlorophenyl)pentane-2-sulfonyl]-4-fluorophenyl)piperazine

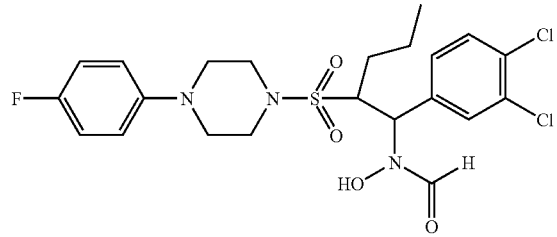

Similarly to Example 1, the syn and anti diastereoisomers of 1-[1-(N-hydroxyamino)-1-(3,4-dichlorophenyl)pentane-2-sulfonyl]-4-(4-fluorophenyl)piperazine were converted to the title compound (as 2 diastereoisomers):

diastereoisomer 1 from the less polar hydroxylamine: 36 mg, 70%; $^1$H-NMR (CDCl$_3$): 8.45 and 8.10 (s, 1H), 7.6-7.2 (m, 3H), 7.0-6.8 (m, 2H), 5.96 and 5.18 (m, 1H), 3.8-3.4 (m, 5H), 2.9-3.15 (m, 4H), 2.0-1.0 (m, 4H), 0.88 and 0.76 (t, 3H, J=7 Hz); MS (ESI): 540 (M{$^{35}$Cl,$^{35}$Cl}Na$^+$), 542 (M{$^{37}$Cl$^{35}$Cl}Na$^+$).

diastereoisomer 2 from the more polar hydroxylamine: 49 mg, 63%; $^1$H-NMR (CDCl$_3$): 8.28 and 8.13 (s, 1H), 7.6-7.2 (m, 3H), 7.0-6.85 (m, 2H), 5.54 and 5.02 (m, 1H), 3.45-3.9 (m, 5H), 3.15 (m, 4H), 1.7-1.2 (m, 4H), 0.76 (t, 3H, J=7 Hz); MS (ESI): 540 (M{$^{35}$Cl,$^{35}$Cl}Na$^+$), 542 (M{$^{37}$Cl,$^{35}$Cl}Na$^+$).

The starting material was prepared as follows:

Similarly to Example 1 i), from 1-(4-fluorophenyl)piperazine and 1-butanesulfonyl chloride was obtained 1-(4-fluorophenyl)-4-(butane-1-sulfonyl)piperazine (1.84 g); similarly to Example 1 ii), this was reacted with 3,4-dichlorobenzaldehyde to give 4-(4-fluorophenyl)-1-[1-(3,4-dichlorophenyl)pent-1-ene-2-sulfonyl]piperazine as a mixture of Z/E isomers (330 mg, 22%): MS (ESI): 457 (M{$^{35}$Cl,$^{35}$Cl}H$^+$), 459 (M{$^{37}$Cl,$^{35}$Cl}H$^+$); similarly to Example 1 iii) except that the mixture was refluxed for 3 days, this was converted to 1-[1-(N-hydroxyamino)-1-(3,4-dichlorophenyl)pentane-2-sulfonyl]-4-(4-fluorophenyl)piperazine as the syn and anti diastereoisomers.

Less polar isomer (50 mg, 15%) (TLC:eluant EtOAc—CH$_2$Cl$_2$—petroleum ether (15-45-50); $^1$H-NMR (CDCl$_3$): 7.53 (d, 1H, J=2.2 Hz), 7.46 (d, 1H, J=7.4 Hz), 7.27 (m, 1H), 6.97 (m, 2H), 6.88 (m, 2H), 4.63 (m, 1H), 3.55 (m, 4H), 3.16 (m, 5H), 1.75 (m, 2H), 1.4 (m, 1H), 1.2 (m, 1H), 0.77 (t, 3H, J=7.4 Hz).

More polar isomer (76 mg, 23%); $^1$H-NMR (CDCl$_3$): 7.52 (d, 1H, J=2 Hz), 7.45 (d, 1H, J=8 Hz), 7.27 (m, 1H), 6.99 (m, 2H), 6.89 (m, 2H), 4.42 (m, 1H), 3.55 (m, 4H), 3.41 (m, 1H), 3.14 (m, 4H), 1.6 (m, 2H), 1.25 (m, 2H), 0.76 (t, 3H, J=7.3 Hz).

Example 10

Trans 1-[2-(N-formyl-N-hydroxyamino)cyclohexane-1-sulfonyl]-4-(4-fluorophenyl)-piperazine

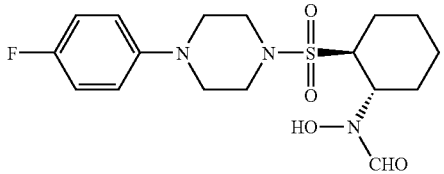

Similarly to Example 1 from trans 1-[2-(N-hydroxyamino)cyclohexane-1-sulfonyl]-4-(4-fluorophenyl)piperazine was obtained the title compound (68 mg, 23%).

$^1$H-NMR (CDCl$_3$): 8.39 and 8.02 (s, 1H), 6.98 (m, 2H), 6.88 (m, 2H), 4.40 and 3.92 (m, 1H), 3.35-3.55 (m, 5H), 3.15 (m, 4H), 2.35 (m, 1H), 2.0-1.8 (m, 3H), 1.2-1.6 (m, 4H); MS (ESI): 408 (MNa$^+$).

The starting material was obtained as follows:

i) To a solution of LDA (51 mmol, prepared by slow addition of n-butyl lithium (20.4 ml, 2.5M in hexane, 51 mmol) to a solution of diisopropylamine (5.16 g, 51 mmol) in THF (30 ml) at −78° C.) at −78° C. was added a solution of 1-(4-fluorophenyl)-4-(methanesulfonyl)-piperazine (6 g, 23.2 mmol) in THF (150 ml). The mixture was stirred for 1 h at −78° C. A solution of 5-chlorovaleryl chloride (4 g, 25.8 mmol) in THF (20 ml) was added dropwise. The mixture was stirred at −78° C. for 1 h and at room temperature for 18 h. The solution was diluted with EtOAc and washed with sat. NH$_4$Cl and brine and dried over MgSO$_4$. Chromatography of the residue on silica gel (eluant:EtOAc—CH$_2$Cl$_2$—petroleum ether (15:35:50)) afforded 1-(6-chloro-2-hexanone-1-sulfonyl)-4-(4-fluorophenyl)piperazine (5.22 g, 60%) as white crystals: MS (ESI): 399 (MNa$^+$).

ii) A mixture of this compound (5.22 g, 13.9 mmol) and NaI (42 g) in acetone (90 ml) was refluxed for 5 h. After cooling and partitioning between EtOAc and water, the organic layer was washed with 10% NaHSO$_3$ and brine, and dried over MgSO$_4$ to give 1-(6-iodo-2-hexanone-1-sulfonyl)-4-(4-fluorophenyl)piperazine (6.13 g, quantitative) as yellowish crystals: $^1$H-NMR (CDCl$_3$): 6.98 (m, 2H), 6.88 (m, 2H), 4.00 (s, 2H), 3.46 (t, 4H, J=4.8 Hz), 3.19 (t, 2H, J=6.6 Hz), 3:16 (t, 4H, J=4.8 Hz), 2.79 (t, 2H, J=6.6 Hz), 1.85 (m, 2H), 1.74 (m, 2H).

iii) A mixture of this compound (1.27 g, 4.85 mmol) and cesium carbonate (8 g, 24.5 mmol) in CH$_2$Cl$_2$ (90 ml) was stirred at room temperature for 4 h. To the mixture was slowly added water and 2N HCl until pH~7. The mixture was extracted with CH$_2$Cl$_2$. The organic layer was dried over MgSO$_4$. Chromatography on silica gel (eluant: EtOAc—petroleum ether (4:6)) afforded 1-(cyclohexanone-2-sulfonyl)-4-(4-fluorophenyl)piperazine (880 mg, 53%).

$^1$H-NMR (CDCl$_3$): 6.97 (m, 2H), 6.88 (m, 2H), 3.83 (m, 1H), 3.48 (m, 4H), 3.12 (m, 4H), 2.81 (m, 1H), 2.54 (m, 1H), 2.46 (m, 1H), 2.2-2.0 (m, 3H), 1.75 (m, 2H); MS (ESI): 363 (MNa$^+$); IR: 1716.

Further elution (EtOAc—petroleum ether (6:4)) afforded 1-[(tetrahydropyran-2-yl)methylidenesulfonyl]-4-(4-fluorophenyl)piperazine (630 mg, 38%): $^1$H-NMR (CDCl$_3$): 6.98 (m, 2H),6.87 (m, 2H), 5.21 (s, 1H), 4.14 (t, 2H, J=5.2 Hz), 3.32 (m, 4H), 3.15 (m, 4H), 2.35 (t, 2H, J=6.6 Hz), 1.82 (m, 4H); MS (ESI): 363 (MNa$^+$).

iv) To a solution of 1-(cyclohexanone-2-sulfonyl)-4-(4-fluorophenyl)piperazine (284 mg, 0.83 mmol) in methanol-THF (16 ml, 3:1) at 0° C. was added sodium borohydride (3.7 mg, 1 mmol). The mixture was stirred at 0° C. for 30 min and at room temperature for 1 h 30. The solvents were evaporated. Saturated NH$_4$Cl and water were added. The precipitate was filtered, washed with water and dried to give 1-(2-cyclohexanol-1-sulfonyl)-4-(4-fluorophenyl)piperazine (250 mg, 88%): MS (ESI): 343 (MH$^+$).

v) To a solution of 1-(2-cyclohexanol-1-sulfonyl)-4-(4-fluorophenyl)piperazine (310 mg, 0.9 mmol) in THF (15 ml) was added triphenylphosphine (1.18 g ; 4.5 mmol) and DEAD (712 μl, 4.5 mmol) dropwise. The mixture was stirred at room temperature for 18 h. Evaporation of the solvents and purification on silica gel (eluant:EtOAc—petroleum ether, gradient from 2:8 to 3:7) gave 1-[1-cyclohexene-1-sulfonyl]-4(4-fluorophenyl)piperazine (285 mg, 98%): MS (ESI): 325 (MH$^+$).

vi) Similarly to Example 1 iii) except that the reaction was heated at 65° C. for 30 h, from 1-(1-cyclohexene-1-sulfonyl)-4-(4-fluorophenyl)piperazine (280 mg, 0.86 mg) was obtained trans 1-[2-(N-hydroxyamino)cyclohexane-1-sulfonyl]-4-(4-fluorophenyl)piperazine (270 mg, 88%): $^1$H-NMR (CDCl$_3$): 6.98 (m, 2H), 6.88 (m, 2H), 3.54 (m, 4H), 3.34 (m, 2H), 3.14 (m, 4H), 2.30 (m, 1H), 2.17 (m, 1H), 2.05 (m, 1H), 1.9-1.2 (m, 5H); MS (ESI): 358 (MH$^+$).

Example 11

Cis 1-[2-(N-formyl-N-hydroxyamino)cyclohexane-1-sulfonyl]-4-(4-fluorophenyl)-piperazine

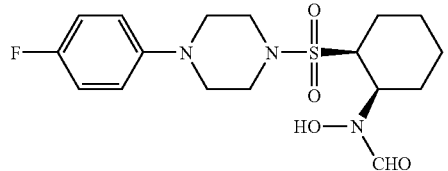

Similarly to Example 1, from cis 1-[2-(N-hydroxyamino)cyclohexane-1-sulfonyl]-4-(4-fluorophenyl)piperazine was obtained the title compound (18 mg, 18%): $^1$H-NMR (CDCl$_3$): 8.39 and 8.07 (s, 1H), 6.98 (m, 2H), 6.88 (m, 2H), 4.77 and 4.25 (m, 1H), 3.48 (m, 5H), 3.13 (m, 4H), 2.25-1.3 (m, 8H); MS (ESI): 408 (MNa$^+$).

The starting material was obtained as follows:

i) A mixture of 1-(cyclohexanone-2-sulfonyl)-4-(4-fluorophenyl)piperazine (50 mg, 0.14 mmol), hydroxylamine hydrochloride (51 mg, 0.73 mmol) and potassium acetate (72 mg, 0.73 mmol) in methanol (5 ml) was heated at 70° C. for 4 h. The solvents were evaporated. After partitioning between EtOAc and water, the organic layer was washed with brine and dried over MgSO$_4$ to give 1-[2-(N-hydroxyimino)cyclohexane-1-sulfonyl]-4-(4-fluorophenyl)piperazine as a white solid (48 mg, 94%): MS (ESI): 356 (MH$^+$).

ii) To this compound (210 mg, 0.6 mmol) in a mixture of THF—acetic acid (7 ml, 1:1) was added sodium cyanoborohydride (276 mg, 4.4 mmol). The mixture was stirred at room temperature for 18 h. Water was added and the pH was adjusted to 9. The mixture was extracted with EtOAc. The organic layer was washed with brine and dried over MgSO$_4$. Chromatography on silica (eluant:EtOAc—petroleum ether, gradient from 1:1 to 8:2) afforded cis 1-[2-(N-hydroxyamino)cyclohexane-1-sulfonyl]-4-(4-fluorophenyl) piperazine (97 mg, 45%): $^1$H-NMR (CDCl$_3$): 6.98 (m, 2H), 6.89 (m, 2H), 3.63 (m, 1H), 3.52 (m, 4H), 3.24 (dt, 1H, $J_d$=10.6 Hz, $J_f$=3.5 Hz), 3.15 (m, 4H), 2.2-1.2 (m, 8H); MS (ESI): 358 (MH$^+$).

Example 12

The following compounds were made using the method outlined in Example 1:

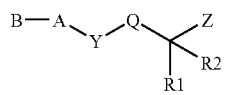

| Mp Low | Mp High | M + H | B | A | Y | Q | R1 | Z |
|---|---|---|---|---|---|---|---|---|
| 117 | 117 | 492-494 | 4-F-Ph | PIP | SO2 | CH2 | 2-(5-Br-thiophene) | RH |
| 128 | 128 | 409 | 4-F-Ph | PIP | SO2 | CH2 | 3-Pyridyl | RH |
| 125 | 125 | 414 | 4-F-Ph | PIP | SO2 | CH2 | 2-thiophenyl | RH |
| 135 | 135 | 414 | 4-F-Ph | PIP | SO2 | CH2 | 3-thiophenyl | RH |
|  |  | 409 | 4-F-Ph | PIP | SO2 | CH2 | 2-Pyridyl | RH |
|  |  | 372 | 4-F-Ph | PIP | CO | N | (S)-PhCH2 | A |
|  |  | 426 | 4-F-Ph | PIP | SO2 | CH2 | 4-F-Ph | RH |
|  |  | 358* | 4-F-Ph | PIP | SO2 | CH2 | Gem-di-Me | RH |
|  |  | 450 | 4-F-Ph | 2-Me-PIP | SO2 | CH2 | PhCH2CH2 | RH |
|  |  | 498* | 4-F-Ph | PIP | SO2 | CH2 | 4-Cl-PhOC(Me)2 | RH |
| 129 | 130 | 389 | 4-Ph | Piperidinyl | SO2 | CH2 | Ph | RH |
|  |  | 500-502 | 3,4-di-Cl-Ph | PIP | SO2 | CH2 | CH2CH(CH3)Ph | RH |
|  |  | 466 | 4-F-Ph | PIP | SO2 | CH2 | PhOCH2CH2CH2 | RH |
| 110 | 110 | 514* | 4-Cl-Ph | PIP | SO2 | CH2 | 4-Cl-PhOC(Me)2 | RH |
| 138 | 140 | 550-552 | 3,4-di-Cl-Ph | PIP | SO2 | CH2 | 4-Cl-PhOC(Me)2 | RH |
| 69 | 70 | 389 | Ph | 4-Piperidinyl | SO2 | CH2 | Ph | RH |
|  |  | 456 | 4-F-Ph | PIP | SO2 | CH2 | c-HexylCH2CH2CH2 | RH |
|  |  | 442 | 4-F-Ph | PIP | SO2 | CH2 | CyclohexylCH2CH2 | RH |
| 139 | 140 | 407 | 4-F-Ph | Piperidinyl | SO2 | CH2 | Ph | RH |
| 172 | 172 | 516 | 4-F-Ph | PIP | SO2 | CH2 | 4-Cl-PhSC(Me)2 | RH |
|  |  | 517-519 | 5-Cl-2-Pyridyl | PIP | SO2 | CH2 | 4-Cl-PhOC(Me)2 | RH |
|  |  | 516-518 | 3-Cl-Ph | PIP | SO2 | CH2 | 4-Cl-PhOC(Me)2 | RH |
|  |  | 505 | 4-F-Ph | PIP | SO2 | CH2 | N-PhCH2-4-Piperidinyl | RH |
| 104 | 104 | 548 | 4-F-Ph | PIP | SO2 | CH2 | 4-Cl-PhSO2C(Me)2 | RH |
| 135 | 135 | 451 | 4-F-Ph | PIP | SO2 | CH2 | 3-PyridylCH(CH3)CH2 | RH |
| 100 | 100 | 451 | 4-F-Ph | PIP | SO2 | CH2 | 4-PyridylCH(CH3)CH2 | RH |
| 65 | 65 | 451 | 4-F-Ph | PIP | SO2 | CH2 | 2-yridylCH(CH3)CH2 | RH |
| 69 | 70 | 449 | 4-F-Ph | Piperidinyl | SO2 | CH2 | PhCH(CH3)CH2 | RH |
| 54 | 55 | 436 | 4-F-Ph | Piperidinyl | SO2 | CH2 | 2-PyridylCH2CH2 | RH |
| 66 | 67 | 449-501 | 4-F-Ph | Piperidinyl | SO2 | CH2 | 4-Cl-PhOC(Me)2 | RH |
|  |  | 480 | 3-Cl-Ph | PIP | SO2 | CH2 | PhCH2CH2CH2CH2 | RH |
| 50 | 55 | 480-482 | 4-Cl-Ph | PIP | SO2 | CH2 | PhCH2CH2CH2 | RH |
|  |  | 450 | 4-F-Ph | PIP | SO2 | CH2 | (S)-2-PhCH(CH3)CH2 | RH |
|  |  | 450 | 4-F-Ph | PIP | SO2 | CH2 | (R)-2-PhCH(CH3)CH2 | RH |
|  |  | 467 | 3-Cl-Ph | PIP | SO2 | CH2 | 3-PyridylCH(CH3)CH2 | RH |
|  |  | 464 | 4-F-Ph | PIP | SO2 | CH2 | CH2CH(CH2CH3)Ph | RH |
| 160 | 163 | 428 | 4-F-Ph | PIP | SO2 | CH2 | CH2c-hexyl | RH |
|  |  | 468 | 5-Cl-2-Pyridyl | PIP | SO2 | CH2 | 3-PyridylCH(CH3)CH2 | RH |
|  |  | 456 | 4-F-Ph | PIP | SO2 | CH2 | 2-thiophenylCH(CH3)CH2 | RH |
| 45 | 46 | 478 | 4-F-Ph | PIP | SO2 | CH2 | PhCH2CH2CH2CH2 | RH |
| 67 | 68 | 450 | 4-F-Ph | PIP | SO2 | CH2 | 2-CH3PhCH2CH2 | RH |
| 75 | 76 | 450 | 4-F-Ph | Piperidinyl | SO2 | CH2 | 3-PyridylCH(CH3)CH2 | RH |
| 69 | 70 | 510-512 | 4-Br-Ph | PIP | SO2 | CH2 | PhCH(CH3)CH2 | RH |
| 133 | 135 | 346 | 4-F-Ph | PIP | SO2 | CH2 | CH3 | RH |
|  |  | 465 | 4-F-Ph | PIP | SO2 | CH2 | CH2CH2CH(CH3)3-Pyr | RH |
| 60 | 63 | 450 | 4-F-Ph | PIP | SO2 | CH2 | CH(CH3)CH2Ph | RH |
|  |  | 478 | 4-F-Ph | PIP | SO2 | CH2 | CH2CH(Pri)Ph | RH |
|  |  | 452 | 4-F-Ph | PIP | SO2 | CH2 | CH2CH(CH3)Pyrazinyl | RH |
|  |  | 420 | 2-Pyrimidinyl | PIP | SO2 | CH2 | PhCH2CH2 | RH |
| 155 | 157 | 454 | 6-Cl-4-Pyrimidinyl | PIP | SO2 | CH2 | PhCH2CH2 | RH |
|  |  | 452 | 4-Cl-Ph | PIP | SO2 | CH2 | PhCH2CH2 | RH |
|  |  | 452 | 3-Cl-Ph | PIP | SO2 | CH2 | PhCH2CH2 | RH |
|  |  | 486 | 3,4-di-Cl-Ph | PIP | SO2 | CH2 | PhCH2CH2 | RH |
|  |  | 453 | 5-Cl-2-Pyridyl | PIP | SO2 | CH2 | PhCH2CH2 | RH |
|  |  | 453 | 3-Cl-2-Pyridyl | PIP | SO2 | CH2 | PhCH2CH2 | RH |
|  |  | 466 | 4-Cl-Ph | Homo-piperazine | SO2 | CH2 | PhCH2CH2 | RH |
|  |  | 419 | 2-Pyridyl | PIP | SO2 | CH2 | PhCH2CH2 | RH |
|  |  | 494 | 6-Cl-4-Pyrimidinyl | PIP | SO2 | CH2 | 3,4-di-Cl-Ph | RH |
|  |  | 450 | 6-MeO-4-Pyrimidinyl | PIP | SO2 | CH2 | PhCH2CH2 | RH |
| 118 | 120 | 470 | 6-Cl-4-Pyrimidinyl | PIP | SO2 | CH2 | PhCH2OCH2 | RH |
|  |  | 493 | 6-Cl-2-Pyridyl | PIP | SO2 | CH2 | 3,4-di-Cl-Ph | RH |
|  |  | 527 | 5-CF3-2-Pyridyl | PIP | SO2 | CH2 | 3,4-di-Cl-Ph | RH |
|  |  | 562 | 3-Cl-5-CF3-2-Pyridyl | PIP | SO2 | CH2 | 3,4-di-Cl-Ph | RH |

-continued

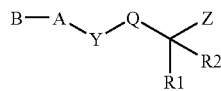

| Mp Low | Mp High | M + H | B | A | Y | Q | R1 | Z |
|---|---|---|---|---|---|---|---|---|
| | | 469 | 5-Cl-2-Pyridyl | PIP | SO2 | CH2 | PhCH2OCH2 | RH |
| | | 493 | 5-Cl-2-Pyridyl | PIP | SO2 | CH2 | 3,4-di-Cl-Ph | RH |
| | | 494 | 6-Cl-4-Pyrimidinyl | PIP | SO2 | CH2 | 4-CF3-Ph | RH |
| | | 523 | 4-Me-2-quinolyl | PIP | SO2 | CH2 | 3,4-di-Cl-Ph | RH |
| | | 468 | 3-Cl-Ph | PIP | SO2 | CH2 | PhCH2OCH2 | RH |
| | | 454 | 2-Cl-4-Pyrimidinyl | PIP | SO2 | CH2 | PhCH2CH2 | RH |
| | | 459 | 2-Benzoxazolyl | PIP | SO2 | CH2 | PhCH2CH2 | RH |
| | | 475 | 2-Benzthiazolyl | PIP | SO2 | CH2 | PhCH2CH2 | RH |
| | | 454 | 6-Cl-3-Pyridazinyl | PIP | SO2 | CH2 | PhCH2CH2 | RH |
| | | 460 | 2-Pyridyl | PIP | SO2 | CH2 | 3,4-di-Cl-Ph | RH |
| | | 459 | 2-Pyridyl | PIP | SO2 | CH2 | 4-CF3-Ph | RH |
| | | 435 | 2-Pyridyl | PIP | SO2 | CH2 | PhCH2OCH2 | RH |
| | | 420 | 2-Pyridyl | PIP | SO2 | CH2 | 2-PyridylCH2CH2 | RH |
| | | 509 | 7-Cl-2-Benzthiazolyl | PIP | SO2 | CH2 | PhCH2CH2 | RH |
| | | 461 | 2-Pyrazinyl | PIP | SO2 | CH2 | 3,4-di-Cl-Ph | RH |
| | | 460 | 2-Pyrazinyl | PIP | SO2 | CH2 | 4-CF3-Ph | RH |
| | | 436 | 2-Pyrazinyl | PIP | SO2 | CH2 | PhCH2OCH2 | RH |
| | | 421 | 2-Pyrazinyl | PIP | SO2 | CH2 | 3-PyridylCH2CH2 | RH |
| | | 420 | 2-Pyrazinyl | PIP | SO2 | CH2 | PhCH2CH2 | RH |
| | | 470 | 6-Cl-3-Pyridazinyl | PIP | SO2 | CH2 | PhCH2OCH2 | RH |
| 136 | 138 | 420 | 4-Pyrimidinyl | PIP | SO2 | CH2 | PhCH2CH2 | RH |
| | | 421 | 2-Pyrazinyl | PIP | SO2 | CH2 | 2-PyridylCH2CH2 | RH |
| | | 417 | 5-Cl-2-Pyridyl | PIP | SO2 | CH2 | c-Pentyl | RH |
| | | 484 | 5-CN-2-Pyridyl | PIP | SO2 | CH2 | 3,4-di-Cl-Ph | RH |
| | | 494 | 6-Cl-2-Benzoxazolyl | PIP | SO2 | CH2 | 2-PyridylCH2CH2 | RH |
| | | | 4-F-Ph | PIP | SO2 | CH2 | 2-Furyl | RH |
| | | 437 | 4-F-Ph | PIP | SO2 | CH2 | 3-PyridylCH2CH2 | RH |
| | | 437 | 4-F-Ph | PIP | SO2 | CH2 | 4-PyridylCH2CH2 | RH |
| | | 492 | 4-F-Ph | PIP | SO2 | CH2 | PhCH2CH2C(Me)2 | RH |
| | | 470, 472 | 4-F-Ph | PIP | SO2 | CH2 | 4-Cl-PhCH2CH2 | RH |
| | | 450 | 4-F-Ph | PIP | SO2 | CH2 | PhCH2CH2CH2 | RH |
| | | 426 | 4-F-Ph | PIP | SO2 | CH2 | 2-FurylCH2CH2 | RH |
| | | 456 | 4-F-Ph | PIP | SO2 | CH2 | 2-Thiophenyl-CH2CH2CH2 | RH |
| | | 468 | 4-F-Ph | PIP | SO2 | CH2 | 4-F-PhCH2CH2CH2 | RH |
| | | 454 | 4-F-Ph | PIP | SO2 | CH2 | 4-F-PhCH2CH2 | RH |
| | | 437 | 4-F-Ph | PIP | SO2 | CH2 | 2-PyridylCH2CH2 | RH |
| | | 509, 511 | 5-Cl-2-Pyridyl | PIP | SO2 | CH2 | 4-Br-2-Thiophenyl | RH |
| | | 420 | 2-Pyridyl | PIP | SO2 | CH2 | 3-PyridylCH2CH2 | RH |
| | | 453, 455 | 3-Cl-Ph | PIP | SO2 | CH2 | 3-PyridylCH2CH2 | RH |
| | | 487, 489 | 3,4-di-Cl-Ph | PIP | SO2 | CH2 | 3-PyridylCH2CH2 | RH |
| | | 464 | 4-F-Ph | PIP | SO2 | CH2 | PhCH2CH2CH2CH2 | RH |
| | | 454, 456 | 5-Cl-2-Pyridyl | PIP | SO2 | CH2 | 3-PyridylCH2CH2 | RH |
| | | 466, 468 | 3-Cl-Ph | PIP | SO2 | CH2 | PhCH2CH2CH2 | RH |
| | | 467, 469 | 5-Cl-2-Pyridyl | PIP | SO2 | CH2 | PhCH2CH2CH2 | RH |
| | | 468, 470 | 6-Cl-4-Pyrimidinyl | PIP | SO2 | CH2 | PhCH2CH2CH2 | RH |
| | | 455, 457 | 2-Cl-4-Pyrimidinyl | PIP | SO2 | CH2 | 3-PyridylCH2CH2 | RH |
| | | 455, 457 | 6-Cl-4-Pyrimidinyl | PIP | SO2 | CH2 | 3-PyridylCH2CH2 | RH |
| | | 454, 456 | 3-Cl-2-Pyridyl | PIP | SO2 | CH2 | 3-PyridylCH2CH2 | RH |
| | | 433 | 2-Pyridyl | PIP | SO2 | CH2 | PhCH2CH2 | RH |
| | | 503 | 5-CF3-2-Pyridyl | PIP | SO2 | CH2 | PhCH2OCH2 | RH |
| | | 468, 470 | P2-Cl-4-Pyrimidinyl | PIP | SO2 | CH2 | PhCH2CH2CH2 | RH |
| | | 453, 455 | 3-Cl-Ph | PIP | SO2 | CH2 | 2-PyridylCH2CH2 | RH |
| | | 487, 489 | 3,4-di-Cl-Ph | PIP | SO2 | CH2 | 2-PyridylCH2CH2 | RH |
| 135 | 137 | 455, 457 | 6-Cl-4-Pyrimidinyl | PIP | SO2 | CH2 | 2-PyridylCH2CH2 | RH |
| 107 | 109 | 488 | 5-CF3-2-Pyridyl | PIP | SO2 | CH2 | 2-PyridylCH2CH2 | RH |
| | | 451 | 4-F-Ph | PIP | SO2 | CH2 | 2-PyridylCH2CH2CH2 | RH |
| 120 | 123 | 452 | 4-F-Ph | PIP | SO2 | CH2 | 2-PyrimidinylCH2CH2CH2 | RH |
| | | 452 | 4-F-Ph | PIP | SO2 | CH2 | 5-PyrimidinylCH2CH2CH2 | RH |
| 119 | 121 | 468 | 5-Cl-2-Pyridyl | PIP | SO2 | CH2 | 2-PyridylCH2CH2CH2 | RH |
| | | 469, 471 | 5-Cl-2-Pyridyl | PIP | SO2 | CH2 | 5-PyrimidinylCH2CH2CH2 | RH |
| 131 | 134 | 469, 471 | 5-Cl-2-Pyridyl | PIP | SO2 | CH2 | 2-PyrimidinylCH2CH2CH2 | RH |
| | | 426, 428 | 5-Cl-2-Pyridyl | PIP | SO2 | CH2 | 2-Pyridyl | RH |

\* = M − H
R2 = hydrogen
PIP = piperazinyl
RH = reverse hydroxamate
A = carboxylic acid MS for C17H24FN3O5S (M+H) calcd 402, found 402.

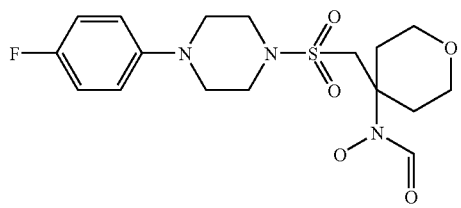

The aryl/heteroarylpiperazines and piperidines used as starting materials were commercially available or were described in the literature, for example
4-(4-fluorophenyl)-piperidine, CAS number 37656-48-7
Piperazine, 1-[1,1'-biphenyl]-4-yl-(180698-19-5)
Piperazine, 1-[1,1'-biphenyl]-3-yl-(115761-61-0)
Piperazine, 1-(2-naphthalenyl)-(57536-91-1)
Piperazinone, 1-phenyl-(90917-86-5)
1H-1,4-Diazepine, 1-(4-chlorophenyl)hexahydro-(41885-98-7)
Quinoline, 4-methyl-2-(1-piperazinyl)-(50693-78-2)
Piperazine, 1-(4-phenoxyphenyl)-62755-61-7
Piperazine, 1-(3-chlorophenyl)-

The 2-methyl-4-(4-fluorophenyl)-piperazine used as starting material was prepared as follows:

Sodium-t-butoxide (4.1 g) was added to a solution of tir-tolylphosphine (0.638 g) and palladium acetate (0.319 g) in toluene (250. mL) under argon and the mixture was stirred for 20 minutes. 4-Fluoro-bromobenzene (5 g) and 2-methylpiperazine (2.85 g) were added and the mixture was heated at 110° C. for 7 hours, then allowed to cool to ambient temperature and keep at this temperature for 20 hours. The reaction mixture was filtered through Celite®, the filter cake was washed twice with dichloromethane (2×25 mL) and the filtrate was evaporated to dryness. The residue was chromatographed on silica eluting initially with dichloromethane and then with a mixture of dichloromethane, methanol and ammonium hydroxide (100:5:1) to give 2-methyl-4(4-fluorophenyl)-piperazine, 2.5 g.

Using this same method and 2,6-dimethylpiperazine as starting material there was obtained 2,6-dimethyl-4-(4-fluorophenyl)-piperazine.

Piperazine, 1-[1,1'-biphenyl-4'-fluoro]-4yl hydrochloride tert-butoxycarbonyl piperazine, 1-[1,1'-biphenyl-4'-fluoro]-4-yl (0.712 g) was stirred in a mixture of dichloromethane (10 ml) and trifluoroacetic acid (1.0 ml) for 18 hours at ambient temperature, evaporated in vacuo to a grey solid and used without further purification. The tert-butoxycarbonyl piperazine, 1-[1,1'-biphenyl-4'-fluoro]-4-yl used as starting material was prepared as follows:

Sodium-t-butoxide (1.35 g) was added to a solution of S-(−)-2,2'-bis(diphenylphosphino)-1,1'-binapthyl (0.46 g) and bis(dibenzylideneacetone)palladium (0.023 g) in toluene (25 ml) under argon and then added 4-bromo-4'-fluorobiphenyl (2.51 g) and 1-tert-butoxycarbonylpiperazine (2.2 g) and the mixture was heated at 80° C. for 5 hours. The reaction mixture was filtered, filtrate evaporated in vacuo to a yellow solid which was triturated and then filtered from diethyl ether(20 ml) to give tert-butoxycarbonyl piperazine, 1-[1,1'-biphenyl-4'-fluoro]-4-yl, (2.67 g), mp 165-166° C.

NMR (d6-DMSO) 1.42 (s, 9H), 3.15 (m, 4H), 3.48 (m, 4H), 7.02 (d, 2H), 7.22 (m, 2H), 7.51 (d, 2H), 7.63 (m, 2H); m/z 357(M+1).

Example 13

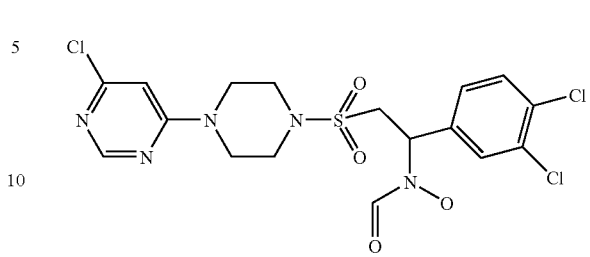

Acetic anhydride (0.23 ml) was added directly to formic acid (0.9 ml). The solution was stirred at room temperature for 30 minutes and then added a solution of N-[2-{[4-(6-chloropyrimidin-4-yl)tetrahydropyrazin-1-yl]sulfonyl}-1-(3,4-dichlorophenyl)ethyl]hydroxylamine (0.227 g) in tetrahydrofuran (5 ml). The solution was stirred at room temperature for 18 hours. The solution was evaporated (water-bath temperature 30° C.) and the residual gum was purified by chromatography using a 10 g silica isolute eluting with CH2Cl2-3% Methanol/CH2Cl2 to give N-[2-{[4-(6-chloropyrimidin-4-yl)piperazino]sulfonyl}-1-(3,4-dichlorophenyl)ethyl]-N-hydroxyformamide (0.178 g), 98-101° C.

NMR (d6-DMSO 373° K.): 3.31 (m, 4H), 3.70 (dd, 1H), 3.75 (m, 4H), 3.95 (dd, 1H), 5.61 (vbs, 1H), 6.89 (s, 1H), 7.43 (dd, 1H), 7.60 (d, 1H), 7.70 (d, 1H), 8.29 (s, 1H), 8.36 (s, 1H);m/z 494 (M+1).

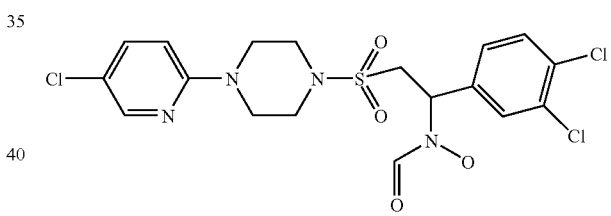

Acetic anhydride (0.63 ml) was added directly to formic acid (2.48 ml). The solution was stirred at room temperature for 30 minutes and then added a solution of N-[2-{[4-5-chloropyridin-2-yl)piperazino]sulfonyl}-1-(3,4-dichlorophenyl)ethyl]hydroxylamine (0.61 g) in tetrahydrofuran (10 ml). The solution was stirred at room temperature for 3 hours and then diluted with ethyl acetate, neutralised the pH with saturated aqueous sodium hydrogen carbonate solution The ethyl acetate layer was separated, dried (Na2SO4), and evaporated to dryness. The residue was purified by chromatography using a 10 g silica isolute eluting with 10% ethyl acetate/heaxane-80% ethyl acetate/hexane and then evaporated to dryness. The resulting white solid was filtered from diethyl ether to give N-[2-{[4-(5-chloropyridin-2-yl)piperazino]sulfonyl}-1-(3,4-dichlorophenyl)ethyl]-N-hydroxyformamide (0.431 g), 211-212° C.

NMR (d6-DMSO 373° K.): 3.30 (m, 4H), 3.80 (mn, 4H), 3.85 (dd, 1H), 3.95 (dd, 1H), 5.58 (vbs, 1H), 6.85 (d, 1H), 7.43 (m, 1H), 7.58 (m, 2H), 7.85 (d, 1H), 8.10 (d, 1H), 8.13 (s, 1H);m/z 493 (M+1).

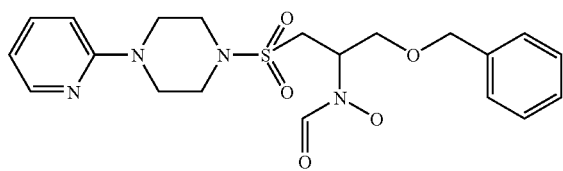

Acetic anhydride (0.48 ml) was added directly to formic acid (1.9 ml). The solution was stirred at room temperature for 30 minutes and then added a solution of N-(2-(benzyloxy)-1-{[(4-pyridin-2-ylpiperazino)sulfonyl]methyl}ethyl) hydroxylamine (0.42 g) in tetrahydrofuran (5 ml). The solution was stirred at room temperature for 3 hours and then diluted with ethyl acetate, neutralised the pH with saturated aqueous sodium hydrogen carbonate solution. The ethyl acetate layer was separated, dried (Na2SO4), and evaporated to dryness. The residue was purified by chromatography using a 10 g silica isolute eluting with CH2Cl25% Methanol/CH2Cl2 to give N-(2-(benzyloxy)-1-{[(4-pyridin-2-ylpiperazino)sulfonyl]methyl-ethyl)-N-hydroxyformamide (0.233 g), 70-75° C.

NMR (d6-DMSO 373° K.): 3.25 (dd, 1H), 3.31 (m, 4H), 3.48 (dd, 1H), 3.65 (m, 4H), 3.66 (dd, 1H), 3.70 (dd, 1H), 4.55 (vbs, 1H), 4.55 (s, 2H), 6.70 (m, 1H), 6.85 (d, 1H), 7.28 (m, H), 7.32 (m, 4H), 7.58 (m, 1H), 8.17 (m, 2H), 9.45 (bs, 1H);m/z 435 (M+1).

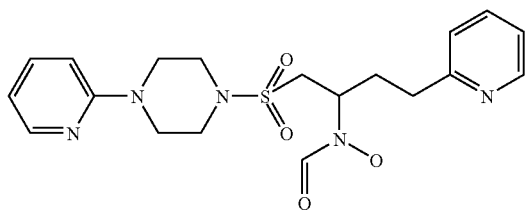

Acetic anhydride (0.48 ml) was added directly to formic acid (1.9 ml). The solution was stirred at room temperature for 30 minutes and then added a solution of N-(3-pyridin-2-yl-1-{[(4-pyridin-2-ylpiperazino)sulfonyl]methyl-propyl) hydroxylamine (0.152 g) in tetrahydrofuran (5 ml). The solution was stirred at room temperature for 3 hours and then diluted with ethyl acetate, neutralised-the pH with saturated aqueous sodium hydrogen carbonate solution The ethyl acetate layer was separated, dried (Na2SO4), and evaporated to dryness. The residue was purified by chromatography using a 10 g silica isolute eluting with CH2Cl25% Methanol/CH2Cl2 to give N-hydroxy-N-(3-pyridin-2-yl-1-{[(4-pyridin-2-ylpiperazino)sulfonyl]methyl}propyl)formamide (0.039 g), 80-84° C.

NMR (d6-DMSO 373° K.):2.10 (m, 2H), 2.80 (m, 2H), 3.25 (dd, 1H), 3.30 (m, 4H), 3.50 (dd, 1H), 3.60 (m, 4H), 4.42 (vbs, 1H), 6.70 (m, 1H), 6.85 (d, 1H), 7.19 (m, 1H), 7.22 (d, 1H), 7.54 (m, 1H), 7.65 (m, 1H), 8.10 (vbs, 1H), 8.15 (m, 1H), 8.45 (m, 1H), 9.50 (vbs, 1H); m/z 420 (M+1).

Example 14

N-{1-[({4-[(5-chloropyridin-2-yl)oxy]piperidino}sulfonyl)methyl]-3-pyridin-3-ylpropyl}-N-hydroxyformamide

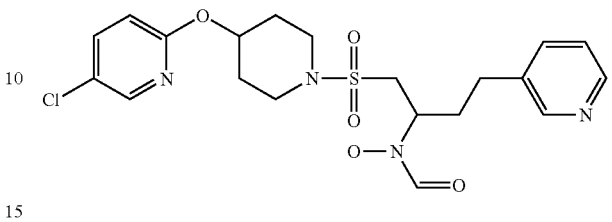

To a solution of 1-N-[2-(hydroxyamino)-2-(3-pyridinyl)butanesulfonyl]-4-O-(5-chloro-2-pyridinyl)piperidine (2.1 g, 4.18 mmol) in THF (36 ml) added a preformed mixture of formic acid (9.0 ml) and acetic anhydride (2.25 ml). The mixture was stirred at room temperature for 18 hrs. The reaction was neutralised using saturated aqueous NaHCO3 before extracting the solution with EtOAc (×2). The combined organics were dried over $Na_2SO_4$ and evaporated in vacuo. The residue was stirred in MeOH at room temperature for 20 hrs to remove the bis-formyl. The residue was crystallised from EtOH to afford a white solid (0.898 g). m.p. 130-140° C.

$^1$H NMR (DMSO-100° C.): 9.50 (br s, 1H), 8.43 (d, 1H), 8.39 (dd, 1H), 8.15 (d, 1H), 8.13 (br s, 1H), 7.74 (dd, 1H), 7.60 (m, 1H), 7.27 (m, 1H), 6.83 (d, 1H), 5.12 (m, 1H), 4.32 (br s, 1H), 3.42 (m, 3H), 3.16 (m, 3H), 2.68-2.54 (m, 2H), 2.06-1.93 (m, 4H), 1.76 (m, 2H); MS. (ES+): 469.2 (MH$^+$), 491.1 (MNa$^+$); EA: calculated for $C_{20}H_{25}ClN_4O_5S$: C 51.22, H 5.37,Cl 7.56, N 11.95, S 6.84, Found: C 50.92, H 5.30, Cl 7.55, N 11.90, S 6.75.

The starting material was prepared as follows:

i) NaH (2.88 g, 66 mmol, 55% dispersion in mineral oil) was stirred in dry DME (200 ml), under Argon. A mixture of 2,5-dichloropyridine (8.87 g, 60 mmol) and 4-hydroxypiperidine (6.67 g, 66 mmol) dissolved in dry DME (200 ml) was added to the NaH suspension dropwise, over a period of 30 minutes. After complete addition the reaction is heated to 82° C. for 48 hrs, maintaining the Argon blanket. The reaction was slowly quenched with water before removing most of the THF. Extracted the aqueous with DCM (×3). The organic layers were dried with $Na_2SO_4$ and evaporated in vacuo to afford 2-(4-piperidinyloxy)-5-chloropyridine as a yellow oil (12.7 g, quantitative). $^1$H NMR (DMSO): 8.17 (d, 1H), 7.76 (dd, 1H), 6.81 (d, 1H), 4.96 (m, 1H), 2.93 (m, 2H), 2.53 (m, 2H), 1.91 (m, 2H), 1.46 (m, 2H); MS (ES+): 213.3 (MH$^+$), 225.3 (MNa$^+$)

ii) To a solution 2-(4-piperidinyloxy) -5-chloropyridine (12.9 g, 0.06 mol) and Et$_3$N (25.4 ml, 0.182 mol) in dry dichloromethane (400 ml) at 0° C. and under Argon, was added methanesulfonyl chloride (5.3 ml, 0.067 mol) in dry dichloromethane (100 ml), dropwise. The mixture was stirred for 20 hours at room temperature. The mixture was diluted with dichloromethane (250 ml), then washed with water (×3) then brine. The organic layers were dried with $Na_2SO_4$ and evaporated in vacuo. The residue was triturated and washed with diethylether to give 2-(N-methanesulfonyl-4-piperidinyloxy)-5-chloropyridine (15.1 g) as a pale yellow solid.

¹H NMR (DMSO): 8.20 (d, 1H), 7.81 (dd, 1H), 6.87 (d, 1H), 5.09 (m, 1H), 3.32 (m, 2H), 3.11 (m, 2H), 2.90 (s, 3H), 2.02 (m, 2H), 1.75 (m, 2H); MS (ES+): 291.2 (MH$^+$), 313.2 (MNa$^+$).

iii) 2-(N-methanesulfonyl-4-piperidinyloxy)-5-chloropyridine (2.0 g, 6.89 mmol) was taken into anhydrous THF (100 ml) under Argon then cooled to −78° C. before the addition of Li(TMSA) (13.8 ml of a 1.0M solution in THF, 13.8 mmol). The mixture was stirred at −78° C. for 20 minutes and a solution of diethylchlorophosphate (1.05 ml, 7.23 mmol) was added. The mixture was stirred at −78° C. for 1 hour before 3-pyridinylpropanal (1.12 g, 8.27 mmol) was added then stirred at −78 for a further 1 hr. The mixture was allowed to warmed to room temperature then was washed with aqueous ammonium chloride and extracted with ethyl acetate. The organic layers were washed with water, brine and dried over Na$_2$SO$_4$. Purification of the residue on silica (eluant:gradient, DCM—2% MeOH/DCM) afforded 2-{N-[E/Z-4(3-pyridyl)-but-1enyl]sulfonyl}-4-piperidinyloxy)-5-chloropyridine as a yellow oil (2.09 g).

¹H NMR (DMSO): 8.45 (m, 1H), 8.37 (m, 1H), 8.19 (m, 1H), 7.82 (m, 1H), 7.64 (m, 1H,), 7.30 (m, 1H), 6.85 (m, 1H), 6.88-6.27 (m, 2H, E/Z isomers), 5.00 (m, 1H), 3.15 (m, 2H), 2.83 (m, 5H), 2.61 (m, 1H), 1.85 (m, 2H), 1.70 (m, 2H); MS (ES+): 408.1 (MH$^+$), 430.2 (MNa$^+$).

iv) To a solution of 2-{N-[E/Z-4(3-pyridyl)-but-1enyl]sulfonyl}-4-piperidinyloxy)-5-chloropyridine(2.09 g, 5.1 mmol) in THF (20 ml) was added hydroxylamine (3.4 ml, 50% aqueous solution). The mixture was stirred for 18 hours. The solvent was evaporated. The residue was dissolved in EtOAc and washed with water (×4). The organic layer was dried on Na$_2$SO$_4$ and evaporated in vacuo to give 2-(4-piperidinyloxy)-5-chloropyridine 1-N-[2-(hydroxyamino)-2-(3-pyridinyl)butanesulfonyl]-4-O-(5-chloro-2-pyridinyl)piperidine (730 mg).

¹H NMR (DMSO): 8.43 (d, 1H), 8.37 (dd, 1H), 8.18 (d, 1H), 7.78 (dd, 1H), 7.61 (m, 1H), 7.36 (s, 1H), 7.29 (m, 1H), 7.85 (d, 1H), 5.70 (s, 1H), 5.08 (m, 1H), 3.35 (m, 3H), 3.16-3.00 (br m, 4H), 2.80-2.60 (br m, 2H), 1.98 (m, 2H), 1.84 (m, 2H), 1.69 (m, 2H); MS (ES+): 441.2 (MH$^+$), 463.2 (MNa$^+$).

Using an analogous procedure to that described in Example X, a aryl-4-O-piperidine was reacted with the appropriate aldehyde to give the compounds listed below.

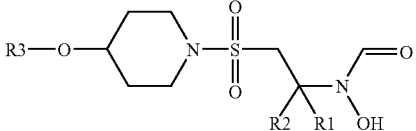

| R1 | R2 | R3 | MW | MS (ES$^+$) |
|---|---|---|---|---|
| Ph | H | 4-chlorophenyl | 438 | 439 |
| PhCH2CH2 | H | 3-chlorophenyl | 466.99 | 468 |
| PhCH2CH2 | H | 3,4-dichlorophenyl | 501.43 | 501 |
| PhCH2CH2 | H | 4-chlorophenyl | 466.99 | 468 |
| PhCH2CH2 | H | 5-chloro-2-pyridyl | 467.98 | 468 |
| PhCH2CH2 | H | 6-chloro-4-pyrimidinyl | 468.96 | 469 |
| Methyl | Methyl | 5-chloro-2-pyridyl | 391.88 | 392 |
| PhCH2CH2 | H | 2-pyridyl | 433.53 | 434 |
| 3-pyridyl | H | 5-chloro-2-pyridyl | 440.91 | 441 |
| 3-pyridylCH2CH2 | H | 5-chloro-2-pyridyl | 468.96 | 469 |

-continued

| R1 | R2 | R3 | MW | MS (ES$^+$) |
|---|---|---|---|---|
| 2-pyridylCH2CH2 | H | 5-chloro-2-pyridyl | 468.96 | 469 |
| PhCH2OCH2 | H | 5-chloro-2-pyridyl | 483.97 | 484 |

The following aryl-4-O-piperidines have been described previously:

Piperidine, 4-(3-chlorophenoxy)-(9Cl), CAS (97840-40-9)
Piperidine, 4-(4-chlorophenoxy)-(9Cl), CAS (97839-99-1)
Pyridine, 2-(4-piperidinyloxy)-(9Cl), CAS (127806-46-6)
Piperidine, 4-(3,4-dichlorophenoxy)-(9Cl) was synthesised in the following alternative route:

1) To a stirred solution 4-hydroxypiperidine(3.5 g, 0.035 mol) in dry methanol (50 ml) at 0° C., was added di-butyl dicarbonate (9.2 ml, 0.042 mol) in dry methanol (50 ml), dropwise. The mixture was stirred for 20 hours at room temperature. The methanol was removed and the remaining solution was taken into Et$_2$O, then washed with 1M citric acid (×3) and water (×3). The combined aqueous extracts were extracted with Et2O which was dried with Na$_2$SO$_4$ and evaporated in vacuo. Purification of the residue on silica (eluant:gradient, DCM—30% MeOH/DCM) afforded N-BOC-4-hydroxypiperidine as a yellow oil (6.4 g). ¹H NMR (DMSO): 4.05 (m, 2H), 3.70-3.52 (br m, 3H), 2.92 (m, 2H), 1.66 (m, 2H), 1.40 s, 9H), 1.33-1.18 (br m, 2H); MS (ES+): 201.3 (MH$^+$), 219.4 (MNH$_4^+$).

2) To a stirred solution N-BOC-4-hydroxypiperidine(2.0 g, 0.01 mol), triphenylphosphine (3.68 g, 0.014 mol) and 3,4-dichlorophenol (1.96 g, 0.012 mol) in dry toluene (75 ml) [with molecular sieves, at 0° C. and under Argon] was added diethyl azodicarboxylate (2.52 ml, 0.016 mol), dropwise. The mixture was stirred for 1.5 hrs at 0° C. Filtered the solution and removed the toluene before vigorously stirring in isohexane (100 ml) and filtered the resulting suspension. The filtrate was washed with 2M aqueous NaOH (×8), dried with Na$_2$SO$_4$ and evaporated in vacuo. Purification of the residue on silica (eluant : 20% EtOAc/isohexane) afforded N-Boc-Piperidine, 4-(3,4-dichlorophenoxy)-(9Cl) as a yellow solid (1.96 g). ¹H NMR (DMSO): 7.52 (d, 1H), 7.31 (d, 1H), 7.01 (dd, 1H), 4.62 (m, 1H), 3.65 (m, 2H), 3.15 (m, 2H), 1.88 (m, 2H), 1.53 (m, 2H), 1.40 (s, 9H); MS (ES+): 346.3 (MH$^+$), 368.4 (MNa$^+$).

3) 50% aquous trifluoroacetic acid (18 ml) was added to a stirred solution N-Boc-piperidine, 4-(3,4-dichlorophenoxy)-(9Cl) (1.96 g, 5.66 mmol). After 3.5 hrs toluene is added and evaporated in vacuo, this was repeated twice. The residue was then taken into EtOAc washed with saturated aqueous NaHCO$_3$(×3), dried with Na$_2$SO$_4$ and evaporated in vacuo to afforded piperidine, 4-(3,4-dichlorophenoxy)(9Cl) a white solid (1.3 g). ¹H NMR (DMSO): 7.54 (d, 1H), 7.35 (d, 1H), 7.04 (dd, 1H), 4.70 (m, 1H), 3.31 (m, 2H), 3.09 (m, 2H), 2.08 (m, 2H), 1.80 (m, 2H); MS (ES+): 2.26.3 (MH$^+$).

Piperidine, 4-(3,4-dichlorophenoxy)-(9Cl) was then taken through steps ii-iv as described above.

Example 15

1-Mesyl-4-(5-methoxycarbonyl-2-pyridyl)piperazine

1-Mesylpiperazine hydrochloride (4.24 g) was added to a solution of methyl 6-chloronicotinate (1.7 g) and N,N-diisopropylethylamine (6.3 ml) in dimethylacetamide (20 ml) and the mixture was heated at 120° C. for 2 hours. The mixture was allowed to cool to ambient temperature and poured onto crushed ice/water (50 ml) to precipitate a tan solid. The solid was collected by filtration and dried at 80° C. for 18 hours in a vacuum oven, to give 1-mesyl-4-(5-methoxycarbonyl-2-pyridyl)piperazine (2.05 g), mp 205-207° C.

NMR (d6-DMSO): 2.90 (s, 3H), 3.20 (m, 4H), 3.78 (m, 3H), 3.80 (s, 3H), 6.92 (d, 1H), 8.00 (dd, 1H), 8.67 (d, 1H); m/z 300 (M+1).

Using an analogous procedure 1-mesylpiperazine hydrochloride, CAS(161357-89-7), was reacted with the appropriate chloropyridine to give the following compounds.

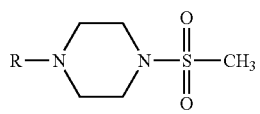

| R | MW | m/z (M + 1) |
|---|---|---|
| 6-Cl-2-pyridyl | 275 | 276 |
| 5-Cl-2-pyridyl | 275 | 276 |
| 5-CF$_3$-2-pyridyl | 309 | 310 |
| 3-Cl-5-CF$_3$-2-pyridyl | 343 | 344 |
| 5-CN-2-pyridyl | 266 | 267 |
| 3-Cl-2-pyridyl | 275 | 276 |
| 5-Br-2-pyridyl | | 320/322 |

1-(6-chloropyrimidin-4-yl)-4-mesylpiperazine

A mixture of 4,6-dichloropyrimidine (39.4 g), 1-mesylpiperazine hydrochloride (55.7 g) and triethylamine (116 ml) in ethanol (500 ml) was stirred at reflux temperature for 4 hours. The mixture was then stirred at room temperature for 12 hours. The solid, which had separated, was collected by filtration, slurry washed with ethanol (2×80 ml, 160 ml) then with diethyl ether (150 ml), and dried to give 1-(6-chloropyrimidin-4-yl)-4-mesylpiperazine as a cream solid (71.9 g). mp 200-202° C.

NMR (d6-DMSO): 2.88 (s, 3H), 3.18 (m, 4H), 3.80 (m, 4H), 7.04 (s, 1H), 8.38 (m, 1H); m/z 277.3 (M+1).

Using an analogous procedure 1-mesylpiperazine hydrochloride, CAS(161357-89-7), was reacted with the appropriate chloropyrimidine or chloropyridazine to give the following compounds.

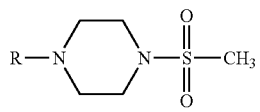

| R | MW | m/z (M + 1) |
|---|---|---|
| 2-Cl-pyrimidin-4-yl | 276 | 277 |
| 6-Cl-pyridazin-3-yl | 276 | 277 |
| pyrimidin-4-yl | 242 | 243 |
| 6-methoxy-pryrimidin-4-yl | | 273.1 |

Example 16

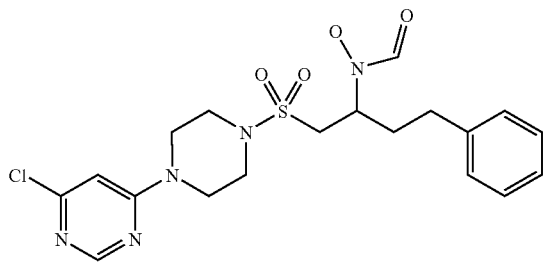

Acetic anhydride (19 ml) was added directly to formic acid (76 ml). The solution was stirred at room temperature for 30 minutes. A solution of 1-(6-chloropyrimidin-4-yl)-4-{[2-(hydroxyamino)-4-phenylbutyl]sulphonyl}piperazine (17.2 g) in tetrahydrofuran (85 ml) was added in portions, to the above solution at 27° C. over 25 minutes. The solution was stirred at room temperature for 1 hour. The solution was evaporated (water-bath temperature 30° C.) and the residual gum was dissolved in ethyl acetate (500 ml). This solution was treated with saturated aqueous sodium hydrogen carbonate solution (200 ml) and the mixture (pH8) was stirred at room temperature for 16 hours. The ethyl acetate layer was separated, washed with saturated brine (100 ml), dried (Na$_2$SO$_4$), and evaporated to dryness. The residual foam was dissolved in ethanol, a solid separated and the mixture was stirred for 2 days. The solid was collected by filtration, slurry washed with diethyl ether (100 ml), and dried to give N-[1-({[4-(6-chloropyrimidin-4-yl)piperazino]sulphonyl}methyl)-3-phenylpropyl]-N-hydroxyformamide as a colourless solid (12.8 g). mp 155-157° C.

Found C, 50.29, H, 5.29, Cl, 7.82, N, 15.31, and S, 6.82%. C$_{19}$H$_{24}$ClN$_5$O$_4$S requires C, 50.27, H, 5.33, Cl, 7.81, N, 15.43, and S, 7.06%. NMR (d6-DMSO 373° K.): 1.93 (m, 1H), 2.03 (m, 1H), 2.57 (m, 1H), 2.65 (m, 1H), 3.20 (dd, 1H), 3.26 (t, 4H), 3.48 (dd, 1H), 3.74 (t, 4H), 4.3 (v br, 1H), 6.90 (s, 1H), 7.19 (m, 3H), 7.27 (m, 2H), 8.1 (br, 1H), 8.38 (s, 1H), 9.5 (s, 1H); m/z 454.2 (M+1).

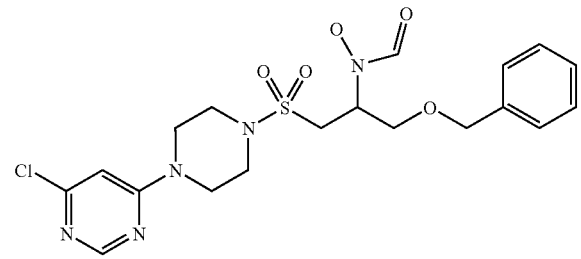

Acetic anhydride (31.5 ml) was added directly to formic acid (126 ml). The solution was stirred at room temperature for 30 minutes.

A solution of 1-{[3-benzyloxy-2-(hydroxyamino)propyl]sulphonyl}-4-(6-chloropyrimidin-4-yl)piperazine (29.5 g) in tetrahydrofuran (150 ml) and formic acid (25 ml), was added in portions to the above solution at 25° C. over 25 minutes. The solution was stirred at room temperature for 1 hour. The solution was evaporated (water-bath temperature 30° C.) and the residual gum was dissolved in ethyl acetate (500 ml). This solution was treated with saturated aqueous sodium hydrogen carbonate solution (2×250 ml) and the mixture (pH8) was stirred at room temperature for 16 hours. The ethyl acetate layer was separated, washed with saturated brine (100 ml), dried (Na₂SO₄), and evaporated to dryness. The residual foam was dissolved in methanol (70 ml) and the solution was stirred for 16 hours. The solution was evaporated to dryness (water-bath temperature 30° C.). The residual foam was stirred in ethanol (250 ml), solid separated and the mixture was stirred for 18 hours. The solid was collected by filtration, slurry washed with diethyl ether (100 ml), and dried to give N-[2-(benzyloxy)1-({[4-(6-chloropyrimidin-4-yl)piperazino]sulphonyl}methyl)ethyl]-N-hydroxyformamide (25.5 g). mp 118-120° C.

Found C, 48.35, H, 5.09, Cl, 7.26, N, 14.73, and S, 6.78%. $C_{19}H_{24}ClN_5O_5S$ requires C, 48.56, H, 5.15, Cl, 7.54, N, 14.90, and S, 6.82%.

NMR (d6-DMSO 373° K.): 3.23 (dd, 1H), 3.30 (t, 4H), 3.46 (dd, 1H), 3.57 (dd, 1H), 3.67 (dd, 1H), 3.72 (t, 4H), 4.50 (s, 2H), 4.50 (m, 1H), 7.35 (m, 5H), 8.15 (br, 1H), 8.38 (s, 1H), 9.48 (br, 1H); m/z 470.2 (M+1).

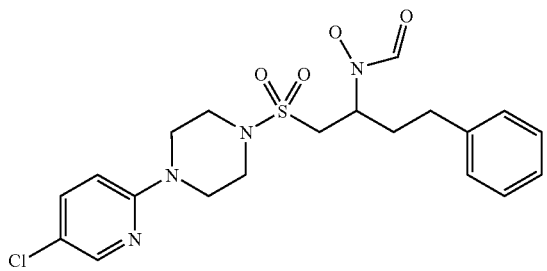

Acetic anhydride (0.8 ml) was added directly to formic acid (3.2 ml). The solution was stirred at room temperature for 30 minutes.

A solution of 1-(5-chloro-2-pyridyl)-4-{[2-(hydroxyamino)-4-phenylbutyl]sulphonyl}piperazine (0:72 g) in tetrahydrofuran (5 ml) was added to the above solution at room temperature. The solution was stirred at room temperature for 2 days. The solution was evaporated (water-bath temperature 40° C.).

The residue was dissolved in 5% methanol in dichloromethane. Silica (5 g Merck 9385) was added to the solution, the mixture was stirred for 21 hours, and evaporated to dryness. The material (pre-adsorbed on the silica) was purified by chromatography on silica (Bond Elut 10 g), using 0-3% methanol in dichloromethane as eluent, to give N-[1-({[4-(5-chloro-2-pyridyl)piperazino]sulphonyl}methyl)-3-phenylpropyl]-N-hydroxyformamide as an orange foam (0.17 g).

NMR (d6-DMSO 373° K.): 1.92 (m, 1H), 2.04 (m, 1H), 2.55 (m, 1H), 2.64 (m, 1H), 3.20 (dd, 1H), 3.27 (m, 4H), 3.47 (dd, 1H), 3.58 (m, 4H), 4.35 (v br, 1H), 6.88 (dd, 1H), 7.17 (m, 3H), 7.27 (m, 2H), 7.57 (dd, 1H), 8.10 (s, 1H), 8.10 (br, 1H), 9.5 (s, 1H); m/z 453.3 (M+1).

Example 17

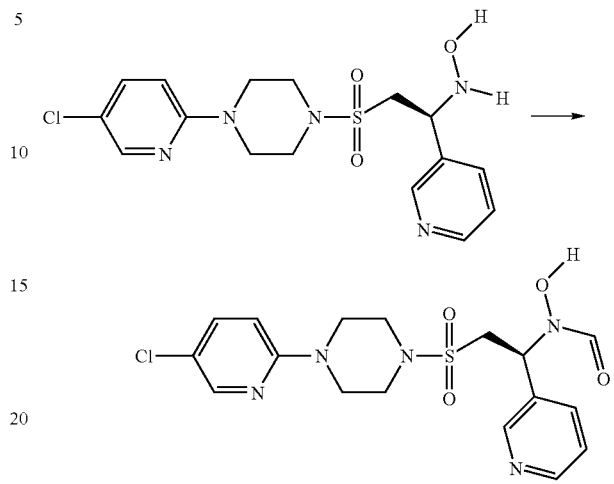

To formic acid (31.5 ml) at 0° C. was added acetic anhydride (7.9 ml). After 20 minutes this was added to the hydroxylamine (6.10 g) dissolved in THF (80 ml) and formic acid (40 ml) and the resulting solution stirred overnight at room temperature. The solvent was removed under reduced pressure and the residue dissolved in DCM (500 ml), washed with saturated sodium bicarbonate solution (2×500 ml), dried and evaporated to dryness. To the residue dissolved in DCM (10 ml) was added diethyl ether (100 ml) to give the product as a white solid (5.60 g) which was collected by filtration. Mpt 168-170° C. NMR DMSOd₆ d 10.2 (br s, 1H)*; 9.8 (br s, 1H)*; 8.7 (br s, 1H)*; 8.6 (br s, 1H)*; 8.5 (d, 1H); 8.3 (m, 1H); 8.1 (d, 1H); 7.9-7.8 (m, 1H); 7.6 (dd, 1H); 7.4 (dd, 1H); 6.9 (d, 1H); 5.8 (m, 1H)*; 5.5 (m, 1H)*; 4.1-3.6 (m, 2H); 3.6 (m, 4H); 3.2 (m, 4H). Anal. Calcd for $C_{17}H_{20}ClN_5O_4S$: C, 48.0; H, 4.7; Cl, 8.3; N, 16.5; S, 7.5. Found: C, 47.9; H, 4.7; Cl, 8.4; N, 16.3; S, 7.5. MS for $C_{17}H_{20}ClN_5O_4S$ (M+H) calcd 426, found 426.

*rotameric signals

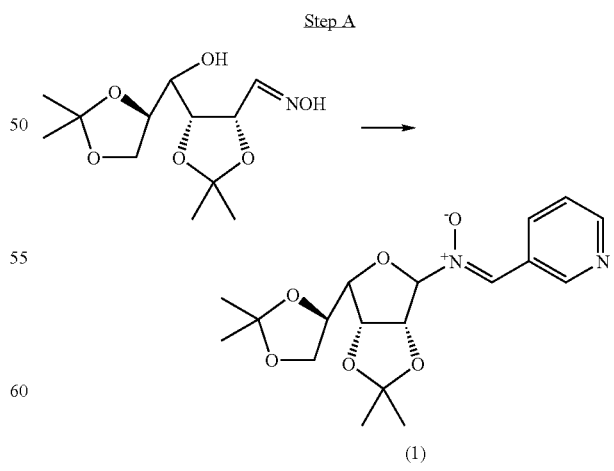

The oxime (31.05 g) [Tetrahedron Letters 1994, 35, 1011] was dissolved in DCM (500 ml) and 3-pyridinecarboxaldehyde (12.09 g) was added followed by anhydrous magnesium sulfate (13.6 g). After 2 days stirring at room temperature more magnesium sulfate (13.6 g) was added and stirring was continued for a further 3 days. The mixture was then filtered, the solvent evaporated and the residue triturated with diethyl ether to give the product (36.34 g) as a white solid. Mpt 174-175° C. NMR CDCl$_3$ d 9.0 (s, 1H); 8.9 (d, 1H); 8.7 (d, 1H); 7.7 (s, 1H); 7.4 (dd, 1H); 5.6 (s, 1H); 5.3 (d, 1H); 4.9 (dd, 1H); 4.6 (dd, 1H); 4.4 (ddd 1H); 4.2 (dd, 1H); 3.7 (dd, 1H); 1.5 (s, 3H); 1.4 (s, 3H); 1.4(s, 3H); 1.3 (s, 3H).

solid. Mpt 209-211° C. (dec). NMR CDCl$_3$ d 8.6 (s, 1H); 8.4 (d, 1H); 8.1 (d, 1H); 7.8 (d, 1H); 7.5 (br s, 1H); 7.4 (dd, 1H); 7.3 (dd, 1H); 6.6 (d, 1H); 4.9 (d, 1H); 4.8 (s, 1H); 4.74.6 (m, 2H); 4.2-4.1 (m, 3H); 3.8 (dd, 1H); 3.6 (dd, 1H); 3.5-3.4 (m, 5H); 3.3-3.2 (m, 4H); 1.4 (s, 3H); 1.3 (s, 3H); 1.3 (s, 3H); 1.3 (s, 3H).

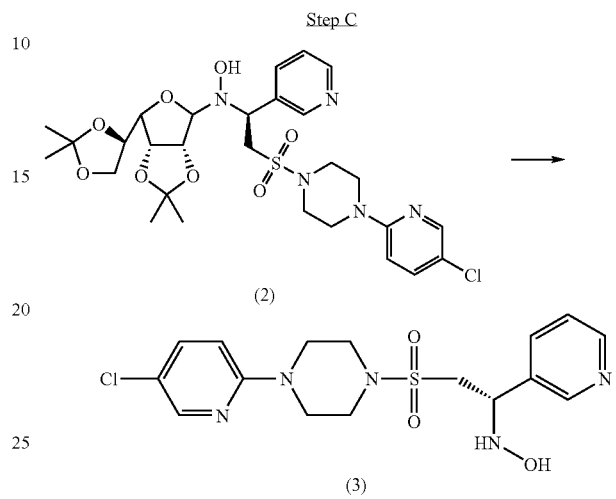

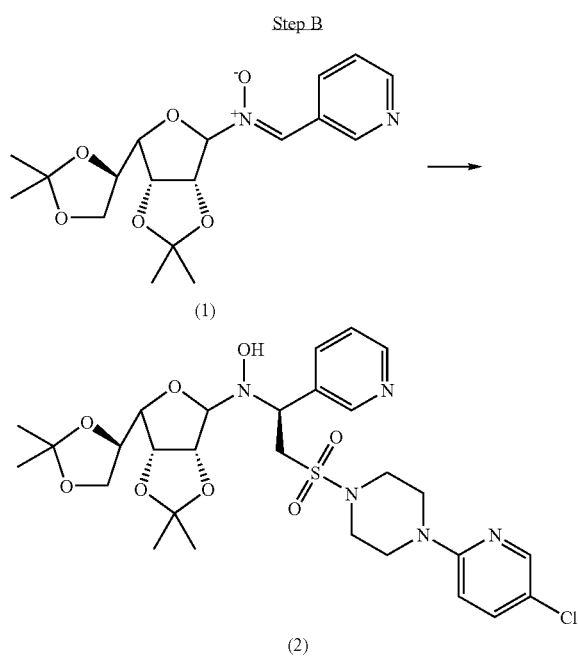

The methyl sulfonamide (14.30 g) was dissolved in THF (500 ml) and cooled to –10° C. when lithium hexamethyldisylazide (78 ml, 1.0M in THF) was added. After 30 minutes the solution was cooled to –78° C., and the nitrone (18.00 g) dissolved in THF (350 ml) was added, keeping the temperature below –65° C. The resulting solution was stirred for 3 hours at –78° C. when it was quenched by the addition of brine (500 ml) and the aqueous layer extracted with ethyl acetate (3×500 ml). The combined organic layers were dried and evaporated to give a yellow solid which was triturated with ethyl acetate/isohexane (4:1) and then purified by flash column chromatography eluting with dichloromethane/methanol (97:3) to give 1 (16.40 g) as a white To a solution of hydroxylamine 2 (14.90 g,) in ethanol (300 ml) was added water (220 ml) followed by O-benzylhydroxylamine hydrochloride (13.91 g) and sodium bicarbonate (6.95 g). Heating gave a solution which was stirred overnight at 80° C. The ethanol was removed under reduced pressure and the residue separated between water (500 ml) and ethyl acetate (500 ml). The aqueous layer was washed with ethyl acetate (2×500 ml), and the combined organic layers were dried and evaporated to give a residue which was triturated with dichloromethane (100 ml) to give 3 (6.10 g) as a white solid. The mother liquor was purified by flash column chromatography eluting with ethyl acetate followed by dichloromethane/methanol (96:4) to give further 3 (0.85 g). Mpt 170-173° C. NMR DMSOd$_6$ d 8.6 (s, 1H); 8.5 (d, 1H); 8.1 (d, 1H); 7.8 (d, 1H); 7.6 (dd, 1H); 7.6 (s, 1H); 7.3 (dd, 1H); 6.9 (d, 1H); 6.1 (br s, 1H); 4.3 (br s, 1H); 3.7-3.4 (m, 6H); 3.2-3.1 (m, 4H).

Example 18

The following compounds were made using the method outlined in Example 7

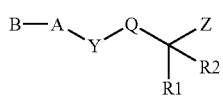

| Mp Low | Mp High | M + H | B | A | Y | Q | R1 | Z |
|---|---|---|---|---|---|---|---|---|
| | | 403 | 4-PhCH2 | Piperidinyl | SO2 | CH2 | Ph | RH |
| | | 357 | 4-HCOO | Piperidinyl | SO2 | CH2 | Ph | RH |

-continued

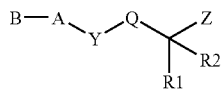

| Mp Low | Mp High | M + H | B | A | Y | Q | R1 | Z |
|---|---|---|---|---|---|---|---|---|
| | | | PhNCO | Piperidinyl | SO2 | CH2 | Ph | RH |
| 128 | 131 | 412 | t-ButylNCO | Piperidinyl | SO2 | CH2 | Ph | RH |
| 122 | 124 | 446 | PhCH2NCO | Piperidinyl | SO2 | CH2 | Ph | RH |
| 129 | 131 | 423 | c-PentylNCO | Piperidinyl | SO2 | CH2 | Ph | RH |
| | | 390 | Ph | PIP | SO2 | CH2 | Ph | RH |
| | | 420 | 4-MeO-Ph | PIP | SO2 | CH2 | Ph | RH |
| | | 435 | 4-NO2-Ph | PIP | SO2 | CH2 | Ph | RH |
| | | 404 | 4-CH3-Ph | PIP | SO2 | CH2 | Ph | RH |
| | | 424 | 2-Cl-Ph | PIP | SO2 | CH2 | Ph | RH |
| | | 420 | 2-OMe-Ph | PIP | SO2 | CH2 | Ph | RH |
| | | 424 | 3-Cl-Ph | PIP | SO2 | CH2 | Ph | RH |
| | | 458 | 3-CF3-Ph | PIP | SO2 | CH2 | Ph | RH |
| | | 424 | 4-Cl-Ph | PIP | SO2 | CH2 | Ph | RH |
| | | 420 | 3-OMe-Ph | PIP | SO2 | CH2 | Ph | RH |
| | | 458 | 3,4-di-Cl-Ph | PIP | SO2 | CH2 | Ph | RH |
| | | 438 | 4-Cl-PhCH2 | PIP | SO2 | CH2 | Ph | RH |
| | | 452 | 4-Cl-PhCO | PIP | SO2 | CH2 | Ph | RH |
| | | 472 | 4-F-PhSO2 | PIP | SO2 | CH2 | Ph | RH |
| | | 436 | 5-NO2-2-Pyridyl | PIP | SO2 | CH2 | Ph | RH |
| | | 432 | PhCH2CO | PIP | SO2 | CH2 | Ph | RH |
| | | 504 | 2-NaphthylSO2 | PIP | SO2 | CH2 | Ph | RH |
| | | 467 | 4-Ph-Ph | PIP | SO2 | CH2 | Ph | RH |
| | | 392 | 2-Pyrazinyl | PIP | SO2 | CH2 | Ph | RH |
| | | 391 | 2-Pyridyl | PIP | SO2 | CH2 | Ph | RH |
| | | 396 | Cyclohexyl | PIP | SO2 | CH2 | Ph | RH |
| | | 466 | 3-Ph-Ph | PIP | SO2 | CH2 | Ph | RH |
| | | 458 | 4-CF3-Ph | PIP | SO2 | CH2 | Ph | RH |
| | | 467 | 4-Cl-PhNCO | PIP | SO2 | CH2 | Ph | RH |
| | | 440 | 2-Naphthyl | PIP | SO2 | CH2 | Ph | RH |
| | | 356 | n-Propyl | PIP | SO2 | CH2 | Ph | RH |
| | | 448 | 4-Piperonyl-CH2— | PIP | SO2 | CH2 | Ph | RH |
| | | 460 | 4-t-Butyl-PhCH2— | PIP | SO2 | CH2 | Ph | RH |
| 55 | 60 | 439 | 4-Cl-PhO | Piperidinyl | SO2 | CH2 | Ph | RH |
| | | 391 | 4-Pyridyl | PIP | SO2 | CH2 | Ph | RH |
| | | 484 | 4'-F-4-Ph-Ph | PIP | SO2 | CH2 | Ph | RH |
| | | 482 | 4-Ph-O-Ph | PIP | SO2 | CH2 | Ph | RH |
| | | 404 | 4-Ph | 3-OxoPIP | SO2 | CH2 | Ph | RH |
| | | 449 | 5-CO2Me-Pyridyl | PIP | SO2 | CH2 | Ph | RH |
| | | 501 | 2-PyridylNCO | Piperidinyl | SO2 | CH2 | 3,4-di-Cl-Ph | RH |
| | | 535 | 5-Cl-2-PyridylNCO | Piperidinyl | SO2 | CH2 | 3,4-di-Cl-Ph | RH |
| | | 534 | 4-Cl-PhNCO | Piperidinyl | SO2 | CH2 | 3,4-di-Cl-Ph | RH |
| | | 500 | PhNCO | Piperidinyl | SO2 | CH2 | 3,4-di-Cl-Ph | RH |

\* = M − H
R2 = hydrogen
PIP = piperazinyl
RH = reverse hydroxamate

The starting material was prepared as follows:

The addition of hydroxylamine to 1-trans-β-styrenesulphonyl-piperidine-4(N-phenylcarboxamide) and the subsequent formylation of the product was carried out as described in Example 7.

Dimethylformamide (2 drops) was added to a suspension of 1-trans-β-styrenesulphonyl-piperidine-4-carboxylic acid (0.75 g) and oxalyl chloride (0.23 mL) in dichloromethane (10 mL) and was stirred for 2 hours. The reaction mixture was evaporated to dryness, re-dissolved in dichloromethane (10 mL) and evaporated to dryness again. The residue obtained was dissolved in dichloromethane (4 mL) and a mixture of aniline (0.23 mL) and triethylamine (0.35 mL) was added dropwise. The mixture was stirred for 20 hours and was washed with dilute 2M hydrocholoric acid, water, aqueous saturated sodium bicarbonate solution and water and dried. Removal of the solvent gave 1-trans-β-styrenesulphonyl-piperdine-4-(N-phenylcarboxamide), 0.89 g Using the method described above there were prepared the following 1-trans-β-styrenesulphonyl-piperdine-4-carboxamides

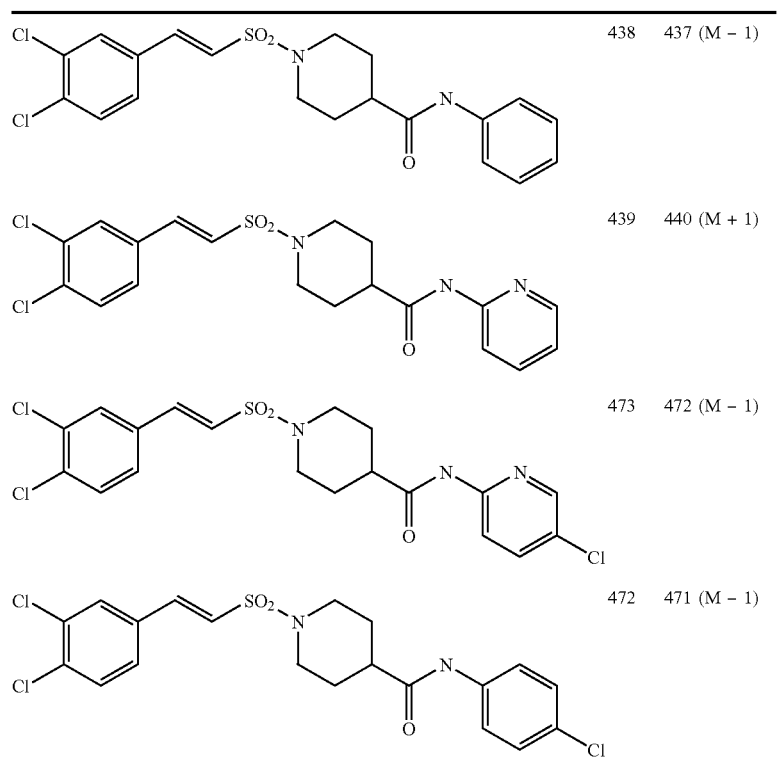

| | | |
|---|---|---|
| (structure) | 438 | 437 (M − 1) |
| (structure) | 439 | 440 (M + 1) |
| (structure) | 473 | 472 (M − 1) |
| (structure) | 472 | 471 (M − 1) |

A solution of ethyl piperidine-4-(carboxylate (3.99 g) in a mixture of THF (30 mL) and methanol (6 mL) was treated with aqueous sodium hydroxide solution (20 mL of 2M NaOH) and the mixture stirred for 3 hours, evaporated to small volume and acidified to pH 5 with dilute 2M hydrochloric acid. The mixture obtained was extracted with ethyl acetate (2×25 mL), the ethyl acetate extracts were washed with water, dried and evaporated to dryness to give 1-trans-β-styrenesulphonyl-piperidine-4-carboxylic acid, 2.64 g.

A solution of ethyl piperidine-4-carboxylate (3.0 mL) and triethylamine (2.7 mL) in dichloromethane (10 mL) was added dropwise to a cooled (ice bath) solution of trans-β-styrenesulphonyl chloride (3.95 g) in dichloromethane (10 mL). The reaction mixture was allowed to warm to ambient temperature and stirring was continued for 20 hours. The reaction mixture was evaporated to dryness, the residue was diluted with water and extracted with ethyl acetate (2×25 mL). The combined ethyl acetate extracts were washed with brine and dried (MgSO4) to give ethyl-(1-trans-β-styrenesulphonyl)-piperidine-4-carboxylate 5.76 g, M+H=324.

An alternative procedure for the preparation of 1-trans-β-3,4dichlorostyrenesulphonyl-piperidine-4-carboxylic acid may be used:

To a solution of 1-trans-β-3,4dichlorostyrenesulphonyl-chloride (2.7 g) and isonipecotic acid (1.41 g) in acetonitrile (15 ml) was added 2M sodium hydroxide (11 ml) and stirred at ambient temperature for 1 hour. The reaction mixture was acidified to pH 3 with 2M hydrochloric acid and extracted with ethyl acetate (2×15 ml), the ethyl acetate extracts were dried (Na2SO4), filtered and evaporated to give 1-trans-β-3,4dichlorostyrenesulphonyl-piperidine-4-carboxylate (2.67 g), n/z 364 (M+1).

Example 19

The following compounds were prepared

| M + H | B | A | Y | Q | R1 | Z |
|---|---|---|---|---|---|---|
| | 4-F-Ph | PIP | SO2 | CH2 | i-Propyl | RH |
| 360 | 4-F-Ph | PIP | SO2 | CH2 | Ethyl | RH |
| 386 | 4-F-Ph | PIP | SO2 | CH2 | spiro-c-pentyl | RH |
| 450.8 | 4-F-Ph | PIP | SO2 | CH2 | 4-NMe2-Ph | RH |
| 442 | 4-F-Ph | PIP | SO2 | CH2 | 4-Cl-Ph | RH |
| 388 | 4-F-Ph | PIP | SO2 | CH2 | tert-Butyl | RH |
| 442 | 4-F-Ph | PIP | SO2 | CH2 | 2-Cl-Ph | RH |
| 484 | 4-F-Ph | PIP | SO2 | CH2 | 4-Ph-Ph | RH |
| 468 | 4-F-Ph | PIP | SO2 | CH2 | 2,4-di-OMe-Ph | RH |
| 452.9 | 4-F-Ph | PIP | SO2 | CH2 | 3-NO2-Ph | RH |
| 475.9 | 4-F-Ph | PIP | SO2 | CH2 | 4-CF3-Ph | RH |
| 475.9 | 4-F-Ph | PIP | SO2 | CH2 | 2-CF3-Ph | RH |
| 374 | 4-F-Ph | PIP | SO2 | CH2 | Propyl | RH |
| 458 | 4-F-Ph | PIP | SO2 | CH2 | 1-Naphthyl | RH |
| 387.9 | 4-F-Ph | PIP | SO2 | CH2 | 3-Furyl | RH |
| 450.9 | 4-F-Ph | PIP | SO2 | CH2 | CH2CH2SCH3 | RH |
| 388 | 4-F-Ph | PIP | SO2 | CH2 | iso-Butyl | RH |
| 491.8 | 4-F-Ph | PIP | SO2 | CH2 | 4-Br-2-Thiophenyl | RH |
| 485.8 | 4-F-Ph | PIP | SO2 | CH2 | 3-Br-Ph | RH |
| 458 | 4-F-Ph | PIP | SO2 | CH2 | 2-Naphthyl | RH |
| 496 | 4-F-Ph | PIP | SO2 | CH2 | 2-Fluorenyl | RH |
| 466 | 4-F-Ph | PIP | SO2 | CH2 | 4-CO2Me-Ph | RH |
| 414 | 4-F-Ph | PIP | SO2 | CH2 | Cyclohexyl | RH |
| 402 | 4-F-Ph | PIP | SO2 | CH2 | 2-neopentyl | RH |
| 533.9 | 4-F-Ph | PIP | SO2 | CH2 | 3-(4-Cl-PhO)-Ph | RH |
| 452 | 4-F-Ph | PIP | SO2 | CH2 | PhCH2OCH2 | RH |
| 507.9 | 4-F-Ph | PIP | SO2 | CH2 | 2-(5-4'-Cl-Ph)Furyl | RH |

-continued

| | | B—A\_Y\_Q\_Z\_R2\_R1 | | | |
|---|---|---|---|---|---|
| M + H | B | A | Y | Q | R1 | Z |
| 450 | 4-F-Ph | PIP | SO2 | CH2 | CH2CH(CH3)Ph | RH |
| 451.9 | 4-F-Ph | PIP | SO2 | CH2 | 4-Piperonyl | RH |
| | 4-F-Ph | PIP | SO2 | CH2 | 3-(OCH2Ph)Ph | RH |
| | 4-F-Ph | PIP | SO2 | CH2 | 4-(OCH2Ph)Ph | RH |
| | 4-F-Ph | PIP | SO2 | CH2 | 3-CF3-Ph | RH |
| 497.9 | 4-F-Ph | PIP | SO2 | CH2 | C6F5 | RH |

PIP = piperazinyl
Z = reverse hydroxamate group
R2 = hydrogen

Example 20

We provide NMR data for the following compounds:

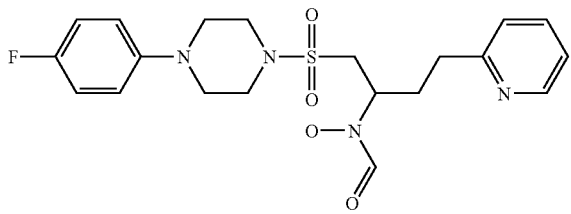

(DMSO) 9.6 (1H, s), 8.5 (1H, m), 8.4 and 7.9 (1H, s), 7.7 (1H, m), 7.2 (2H, m), 7.1 (2H, m), 7.0 (2H, m), 4.7 and 4.2 (1H, broad m), 3.4 (1H, m), 3.3 (5H, m), 3.1 (4H, m), 2.7 (2H, m), 2.1 (2H, m).

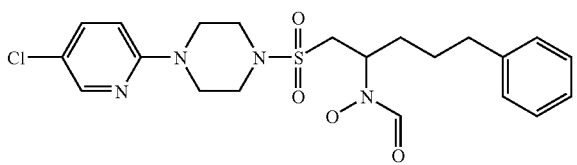

(DMSO) 9,8 and 9.5 (1H, broad s), 8.3 and 8.0 (1H, s), 8.1 (1H, d), 7.6 (1H, dd), 7.2 (5H, m), 6.9 (1H, d), 4.7 and 4.1 (1H broad m), 3.6 (4H, m), 3.4 (1H, m), 3.3 (1H, m), 3.2 (4H, m), 2.6 (2H, m), 1.6 (4H, m).

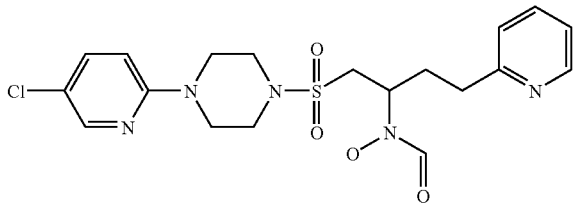

(DMSO) 9.6 (1H, broad S), 8.4 (1H, m), 8.3 and 7.9 (1H, s), 8.1 (1H, d), 7.6 (2H, m), 7.2 (1H, d), 7.1 (1H, m), 6.9 (1H, d), 4.7 and 4.1 (1H, broad m), 3.6 (4H, m), 3.4 (1H, m), 3.3 (1H, m), 3.2 (4H, m), 2.7 (2H, m), 2.0 (2H, m).

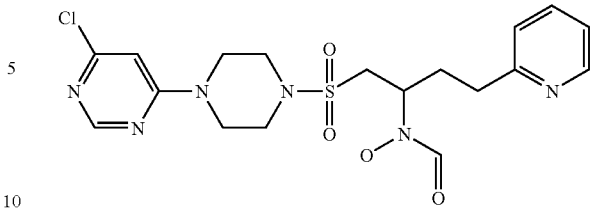

(DMSO) 9.7 (1H, broad s), 8.5 (1H, m), 8.4 (1H, m), 8.1 and 7.9 (1H, s), 7.6 (1H, m), 7.2 (2H, m), 7.0 (1H, m), 4.6 and 4.1 (1H, broad m), 3.7 (4H, m), 3.4 (1H, m), 3.3 (5H, m), 2.7 (2H, m), 2.0 (2H, m).

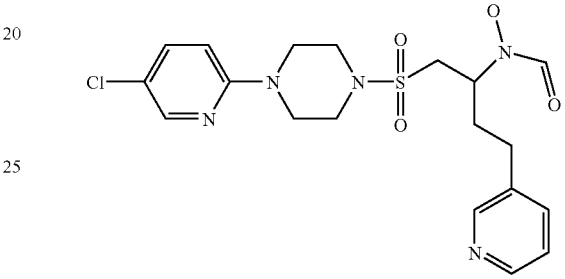

(DMSO) 9.9 (1H, s), 8.4 (2H, m), 8.2 (1H, d), 7.65 (2H, m), 7.3 (1H, m), 7.0 (1H, m), 4.0-4.2 (2H, m), 3.6 (4H, br m), 3.4-3.2 (6H, br m), 2.0 (2H, br m).

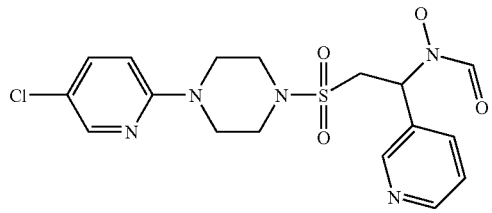

(DMSO) 10.0 (1H, s), 8.5 (2H, d), 8.2 (1H, br s), 7.8 (1H, br), 7.6 (1H, m), 7.4 (1H, m), 6.9 (1H, m), 3.6 (4H, br m), 3.2 (6H, br m).

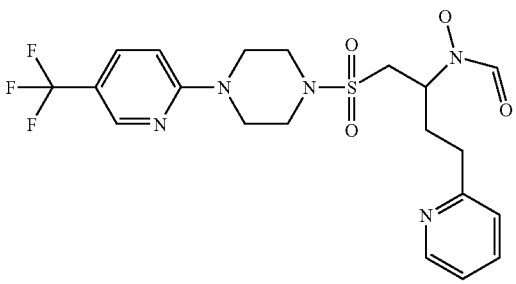

10.0 (1H, s), 8.5 (2H, m), 8.4 and 8.0 (1H, s), 7.9 (1H, m), 7.7 (1H, m), 7.3 (1H, m), 7.1 (1H, m), 3.7 (4H, br m), 3.45 (2H, m), 3.3 (4H, br m), 2.75 (3H, m), 2.1 (2H, m).

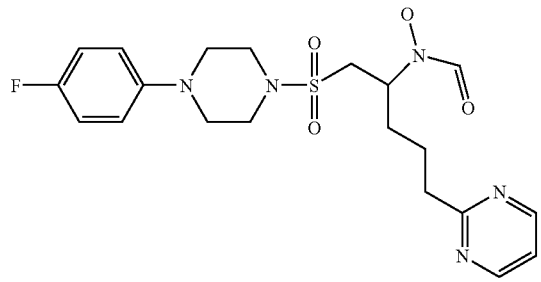

(DMSO) 10.0 (1H, br s), 8.6 (2H, m), 8.2 (1H, d), 7.2 (1H, m), 6.9 (4H, m), 4.9 and 4.2 (1H, br), 3.4 (6H, m), 3.0 (6H, m), 1.9 (4H, m).

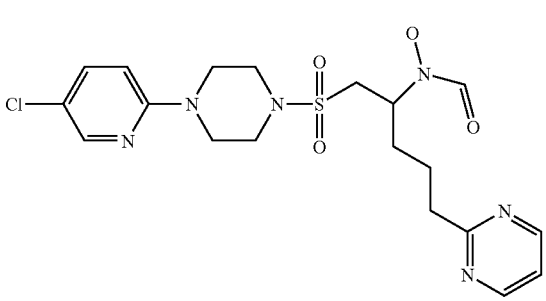

(DMSO) 9.8 (1H, br), 8.7 (2H, m), 8.3 and 7.9 (1H, s), 8.1 (2H, s), 7.6 (1H, m), 7.3 (1H, m), 6.9 (1H, m), 4.1 (1H, br m), 3.6 (4H, m), 3.2 (6H, m), 2.8 (2H, m), 1.8 (4H, m).

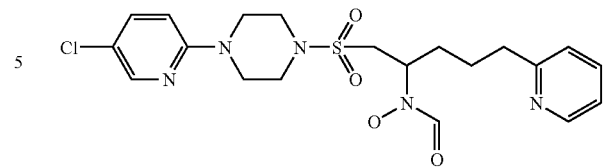

(CDCl$_3$) 8.5 (1H, m), 8.1 (2H, s), 8.5 and 8.0 (1H, s), 7.8 (1H, m), 7.4 (1H, m), 7.3 (2H, m), 6.6 (1H, m), 4.8 and 4.2 (1H, br m), 3.6 (4H, m) 3.2 (6H, m), 2.8 (2H, m), 1.8 (4H, m).

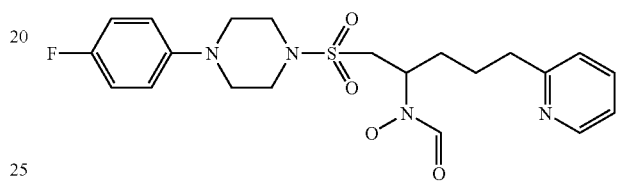

(DMSO) 8.5 (1H, d), 8.4 and 8.2 (1H, s), 7.7 (1H, m), 7.2 (6H, m), 4.8 and 4.2 (1H, br m), 3.6 (4H, m), 3.2 (6H, m), 2.8 (2H, m), 1.8 (4H, m).

Example 21

The following compounds were prepared

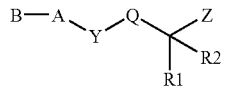

| Mp Low | Mp High | M + H | B | A | Y | Q | R1 | Z |
|---|---|---|---|---|---|---|---|---|
| | | 467 | 4-Cl-Ph | PIP | SO2 | CH2 | 3-PyridylCH(CH3)CH2 | RH |
| 55 | 60 | 456 | 4-F-Ph | PIP | SO2 | CH2 | c hexylC(Me)CH2 | RH |
| 125 | 128 | 440 | 4-F-Ph | PIP | SO2 | CH2 | PhCH2SCH2 | RH |
| 130 | 131 | 460 | 4-F-Ph | Piperidinyl | SO2 | CH2 | 2-IndanCH2 | RH |
| 64 | 65 | 448 | 4-F-Ph | Piperidinyl | SO2 | CH2 | (R)-2-PhCH(CH3)CH2 | RH |
| 63 | 64 | 448 | 4-F-Ph | Piperidinyl | SO2 | CH2 | (S)-2-PhCH(CH3)CH2 | RH |
| 132 | 137 | 484 | 4-F-Ph | PIP | SO2 | CH2 | 2-Cl-PhCH(CH3)CH2 | RH |
| | | 484 | 4-F-Ph | PIP | SO2 | CH2 | 4-Cl-PhCH(CH3)CH2 | RH |
| | | 484 | 4-F-Ph | PIP | SO2 | CH2 | 3-Cl-PhCH(CH3)CH2 | RH |
| | | 469 | 5-Cl-2-Pyridyl | PIP | SO2 | CH2 | 2-PyrazineCH(CH3)CH2 | RH |
| | | 516 | 4-F-Ph | PIP | SO2 | CH2 | 4-Cl-Ph-S-CH(CH3)CH2 | RH |
| | | 466 | 3-Cl-Ph | PIP | SO2 | CH2 | (S)-2-PhCH(CH3)CH2 | RH |
| | | 467 | 5-Cl-2-Pyridyl | PIP | SO2 | CH2 | (S)-2-PhCH(CH3)CH2 | RH |
| 50 | 51 | 450 | 4-F-Ph | Piperidinyl | SO2 | CH2 | 2-PyrazineCH(CH3)CH2 | RH |
| 60 | 61 | 454 | 4-F-Ph | Piperidinyl | SO2 | CH2 | 2-ThiophenylCH(CH3)CH2 | RH |
| 82 | 83 | 449 | 4-F-Ph | Piperidinyl | SO2 | CH2 | 4-PyridylCH(CH3)CH2 | RH |
| 65 | 66 | 407 | 4-F-Ph | PIP | SO2 | CH-Ph | | RH |
| 91 | 100 | 484 | 4-F-Ph | PIP | SO2 | CH2 | PhCH2SOCH2 | RH |
| 142 | 145 | 484 | 4-F-Ph | PIP | SO2 | CH2 | PhCH2SOCH2 | RH |
| | | 455 | 5-Cl-2-Pyridyl | PIP | SO2 | CH2 | 2-PyrimidinylCH2CH2 | RH |
| | | 460 | 5-cyano-2-pyridyl | PIP | SO2 | CH2 | 2-PyrimidinylCH2CH2 | RH |
| | | 444 | 5-cyano-2-pyridyl | PIP | SO2 | CH2 | PhCH2CH2 | RH |
| | | 464 | 5-cyano-2-pyridyl | PIP | SO2 | CH2 | 2-ThiophenylCH2CH2CH2 | RH |
| | | 445 | 5-cyano-2-pyridyl | PIP | SO2 | CH2 | 3-PyridylCH2CH2 | RH |
| | | 459 | 5-cyano-2-pyridyl | PIP | SO2 | CH2 | 2-PyridylCHHH2CH2CH2 | RH |
| | | 460 | 5-cyano-2-pyridyl | PIP | SO2 | CH2 | PhCH2OCH2 | RH |

-continued $$\underset{R1}{\overset{Z}{\underset{R2}{B-A_{Y}Q}}}$$

| Mp Low | Mp High | M + H | B | A | Y | Q | R1 | Z |
|---|---|---|---|---|---|---|---|---|
| | | 445 | 5-cyano-2-pyridyl | PIP | SO2 | CH2 | 2-PyridylCH2CH2 | RH |
| | | 417 | 5-cyano-2-pyridyl | PIP | SO2 | CH2 | 3-Pyridyl | RH |
| | | 498/500 | 5-Br-2-Pyridyl | PIP | SO2 | CH2 | 2-PyridylCH2CH2 | RH |
| | | 498/500 | 5-Br-2-Pyridyl | PIP | SO2 | CH2 | 3-PyridylCH2CH2 | RH |
| | | 497/499 | 5-Br-2-Pyridyl | PIP | SO2 | CH2 | PhCH2CH2 | RH |
| | | 513/515 | 5-Br-2-Pyridyl | PIP | SO2 | CH2 | PhCH2OCH2 | RH |
| | | 470/472 | 5-Br-2-Pyridyl | PIP | SO2 | CH2 | 3-Pyridyl | RH |
| | | 517/519 | 5-Br-2-Pyridyl | PIP | SO2 | CH2 | 2-ThiophenylCH2CH2CH2 | RH |
| | | 513/515 | 5-Br-2-Pyridyl | PIP | SO2 | CH2 | 2-PyrimidinylCH2CH2CH2 | RH |
| | | 512/514 | 5-Br-2-Pyridyl | PIP | SO2 | CH2 | 2-PyridylCH2CH2CH2 | RH |
| | | 436 | 2-Pyrazinyl | PIP | SO2 | CH2 | 2-PyrimidinylCH2CH2CH2 | RH |
| | | 439 | 2-Pyridyl | PIP | SO2 | CH2 | 2-ThiophenylCH2CH2CH2 | RH |
| | | 440 | 2-Pyrazinyl | PIP | SO2 | CH2 | 2-ThiophenylCH2CH2CH2 | RH |
| | | 488.1 | 5-Cl-2-Pyridyl | 4-O-Piperidinyl | SO2 | CH2 | 2-ThiophenylCH2CH2CH2 | RH |
| 103 | 104 | 484.1 | 5-Cl-2-Pyridyl | 4-O-Piperidinyl | SO2 | CH2 | 2-ThiophenylCH2CH2CH2 | RH |
| | | 483.3 | 5-Cl-2-Pyridyl | 4-O-Piperidinyl | SO2 | CH2 | 2-PyridylCH2CH2CH2 | RH |
| | | 508.1 | 5-Cl-2-Pyridyl | 4-O-Piperidinyl | SO2 | CH2 | 3,4-di-Cl-Ph | RH |
| | | 504/506 | 5-Cl-2-Pyridyl | PIP | SO2 | CH2 | 3-Pyridyl-5-bromo | RH |
| 123 | 125 | 466.3 | 6-MeO-4-Pyrimidinyl | PIP | SO2 | CH2 | PhCH2OCH2 | RH |
| 99 | 101 | 451.3 | 6-MeO-4-Pyrimidinyl | PIP | SO2 | CH2 | 2-PyridylCH2CH2 | RH |
| 95 | 99 | 451.4 | 6-MeO-4-Pyrimidinyl | PIP | SO2 | CH2 | 3-PyridylCH2CH2 | RH |
| 156 | 158 | 470.3 | 6-MeO-4-Pyrimidinyl | PIP | SO2 | CH2 | 2-ThiophenylCH2CH2CH2 | RH |
| 122 | 124 | 466.3 | 6-MeO-4-Pyrimidinyl | PIP | SO2 | CH2 | 2-PyrimidinylCH2CH2CH2 | RH |
| | | 465.3 | 6-MeO-4-Pyrimidinyl | PIP | SO2 | CH2 | 2-PyridylCH2CH2CH2 | RH |

PIP = piperazinyl
Z = reverse hydroxamate group
R2 = hydrogen

All compounds were prepared as in Example 1 except those where ring A is 4-O-piperidinyl which were prepared as in Example 14.

Example 22

We provide NMR data for the following compounds listed in Example 21:

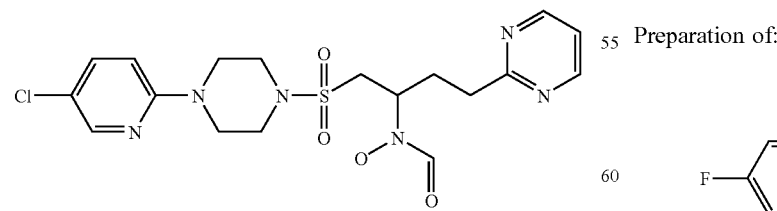

M452587-new compound
NMR (DMSO)9.9,9.6 (1H broad s); 8.6 (2Hm);
8.3 and 7.9 (1H s); 8.1 (1H,dd); 7.3 (1H,m)6.9(1H,d); 4.7 and 4.2 (1H broad,m);
3.6 (4H,m); 3.4-3.2 (6H,m); 2.8 (2H,m); 2.1 (2H,m).

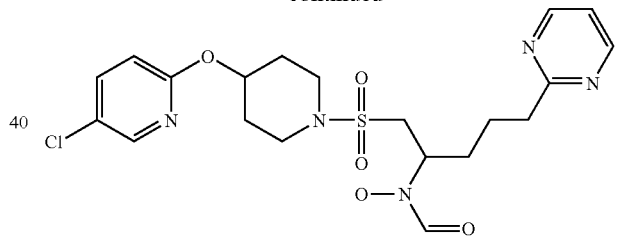

(DMSO)9.9 and 9.6 (1H, broad s), 8.7 (2H, d),
8.3 and 8.0 (1H, s),8.2 (1H, d), 7.8 (1H, dd), 7.3
(1H, m),6.9 (1H, d), 5.1 (1H, broad m),4.7 and
4.1 (1H, broad m), 3.4 (3H, m), 3.1 (3H, m), 4.7 and
4.1 (1H, broad m), 3.4 (3H, m), 3.1 (3H, m), 2.9
(2H, m), 2.0 (2H, m), 1.7 (6H, m).

Example 23

Preparation of:

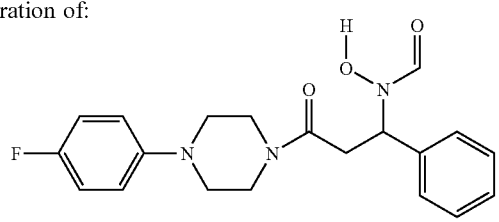

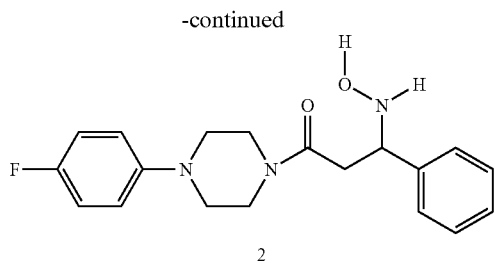

2

To formic acid (4.8 ml) at 0° C. was added acetic anhydride (1.2 ml). After 20 minutes this was added to the hydroxylamine 2 (0.68 g) dissolved in THF (11 ml) and formic acid (5 ml) and the resulting solution stirred overnight at room temperature. The solvent was removed under reduced pressure and the residue dissolved in DCM (100 ml), washed with saturated sodium bicarbonate solution (2×100 ml), dried (MgSO$_4$) and evaporated to dryness. The residue was purified by flash column chromatography eluting with dichloromethane/methanol (96:4) to give the product (0.41 g) as a gum. NMR CDCl$_3$ δ 9.7 (br s, 1H)*; 9.2 (br s, 1H)*; 8.4 (s, 1H)*; 8.0 (s, 1H)*; 7.5-7.2 (m, 5H); 7.0-6.8 (m, 4H); 5.7 (m, 1H)*; 5.4 (m, 1H)*; 3.9-3.4 (m, 5H); 3.3 (m, 1H)*; 3.2-2.9 (m, 4H); 2.8 (m, 1H)*. MS for C$_{20}$H$_{22}$FN$_3$O$_3$ (M+H) calcd 372, found 372.

*rotameric signals

Step A

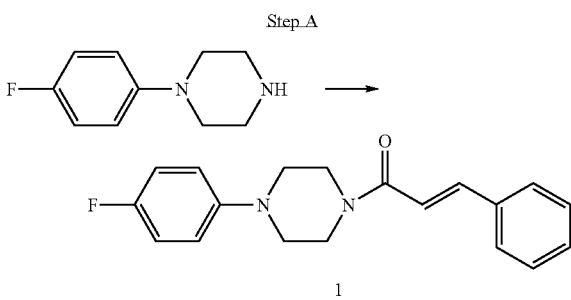

1

To 1-(4-fluorophenyl)piperazine (1.00 g) dissolved in DCM (10 ml) was added cinnamoyl chloride (0.85 g) in DCM (10 ml) followed by triethylamine (1.55 ml). The solution was stirred at room temperature overnight. It was then separated between DCM (150 ml) and water (100 ml), the organic layer was then washed with water (100 ml), dried (MgSO$_4$) and evaporated to dryness to give a cream solid which was triturated with diethyl ether (10 ml) to give 1 (1.20 g) as a white solid. NMR CDCl$_3$δ 7.7 (d, 1H); 7.5 (m, 2H); 7.4 (m, 3H); 7.0-6.9 (m, 5H); 4.0-3.8 (m, 4H); 3.1 (m, 4H). MS for C$_{19}$H$_{19}$FN$_2$O (M+H) calcd 311, found 311.

Step B

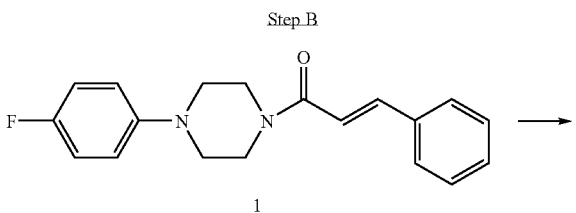

1

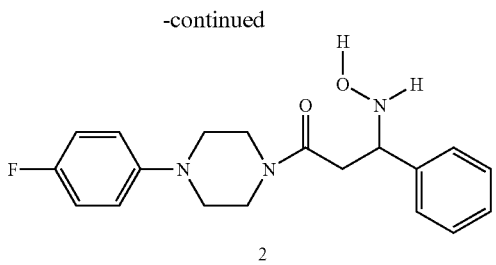

2

To the amide (2.00 g) dissolved in THF (40 ml) was added hydroxylamine (1 ml, 50% aqueous solution). The solution was stirred at room temperature for 48 hours. The solvent was then evaporated under reduced pressure, toluene was added (50 ml) and this was also evaporated under reduced pressure. The residue was triturated with dichloromethane/methanol (98:2) and the mother liquor purified by flash column chromatography eluting with dichloromethane/methanol (98:2) to give 2 (0.70 g) as a gum. NMR CDCl$_3$δ 7.5-7.2 (m, 5H); 7.0-6.9 (m, 2H); 6.9-6.8 (m, 2H); 4.5 (dd, 1H); 3.8-3.7 (m, 2H); 3.6-3.5 (m, 2H); 3.1-2.8 (m, 5H); 2.7 (dd, 1H). MS for C$_{19}$H$_{22}$FN$_3$O$_2$ (M+H) calcd 344, found 344.

What we claim is:

1. A compound of the formula (I)

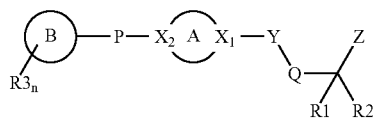

I wherein ring B is a monocyclic or bicyclic heteroaryl ring comprising up to 12 ring atoms and containing one or more heteroatoms independently chosen from N, O, and S; ring B may optionally be linked to ring A by a C1-4 alkyl or a C1-4 alkoxy chain linking the 2-position of ring B with a carbon atom alpha to X$_2$;

each R3 is independently selected from hydrogen, halogen, NO$_2$, COOR wherein R is hydrogen or C1-6 alkyl, CN, CF$_3$, C1-6 alkyl, —S—C1-6 alkyl, —SO—C1-6 alkyl, —SO$_2$—C1-6 alkyl, C1-6 alkoxy and up to C10 aryloxy, n is 1, 2 or 3;

P is —(CH$_2$)$_n$— wherein n=0, 1, or 2; or P is an alkene or alkyne chain of up to six carbon atoms; or where X$_2$ is C, P is -Het-, —(CH[R6])$_n$-Het-, -Het-(CH[R6])$_n$- or -Het-(CH[R6])$_n$-Het-, wherein Het is selected from —CO—, —S—, SO—, —SO$_2$—, —NR6—, or —O— wherein n is 1 or 2; or P is selected from —CO—N(R6)—, —N(R6)—CO—, —SO$_2$—N(R6)— and N(R6)—SO$_2$—, and R6 is hydrogen, C1-6 alkyl, up to C10 aralkyl or up to C9 heteroalkyl;

Ring A is a piperidine ring and may optionally be mono- or di-substituted by optionally substituted C1-6 alkyl or C1-6 alkoxy, each substituent being independently selected from halogen, C1-6 alkyl or an oxo group;

X$_1$ and X$_2$ are independently selected from N and C, such that only one of X$_1$ and X$_2$ is N, and the other is C;

Y is selected from —SO$_2$— and —CO—;

Z is —CONHOH, Y is —CO— and Q is selected from —C(R6)(R7)—, —C(R6)(R7)—CH$_2$—, —N(R6)—, and —N(R7)—CH2— wherein R6 is as defined above, and solely in relation to Q as here defined, R6 may also represent up to C10 aryl and up to C9 heteroaryl, and R7 is H, C1-6 alkyl, or together with R6 forms a carbocyclic or heterocyclic spiro 5-, 6- or 7-membered ring, the latter containing at least one heteroatom selected from N, O, and S;

Z is —CONHOH, Y is —SO$_2$— and Q is selected from —C(R6)(R7)—, and —C(R6)(R7)—CH$_2$—; or Z is —N(OH)CHO and Q is selected from —CH(R6)—, —CH(R6)—CH$_2$—, and —N(R6)—CH$_2$—;

R1 is H, C1-6 alkyl, C5-7 cycloalkyl, up to C10 aryl, up to C10 heteroaryl, up to C12 aralkyl, or up to C12 heteroarylalkyl, all optionally substituted by up to three groups independently selected from NO$_2$, CF$_3$, halogen, C1-4 alkyl, carboxy(C1-5)alkyl, up to C6 cycloalkyl, —OR4, —SR5, C1-4 alkyl substituted with —OR4, —SR4, NR4, N—Y—R4, or C1-4 alkyl-Y—NR4, with the proviso that where R1 is —OH, —OR4, —SR4, or NR4, or N—Y—R4 then Z is not —N(OH)CHO, or R1 is 2,3,4,5,6-pentafluorophenyl;

R4 is hydrogen, C1-6 alkyl, up to C10 aryl or up to C10 heteroaryl or up to C9 aralkyl, each independently optionally substituted by halogen, NO$_2$, CN, CF$_3$, C1-6 alkyl, —S—C1-6 alkyl, —SO—C1-6 alkyl, —SO2—C1-6 alkyl or C1-6 alkoxy;

R2 is H, C1-6 alkyl, or together with R1 forms a carbocyclic or heterocyclic spiro 5-, 6- or 7-membered ring, the latter containing at least one heteroatom selected from N, O, and S; also the group Q can be linked to either R1 or R2 to form a 5-, 6- or 7-membered alkyl or heteroalkyl ring comprising one or more of O, S and N; and wherein any alkyl groups outlined above may be straight chain or branched, or a pharmaceutically acceptable salt or in vivo hydrolysable precursor thereof.

2. A compound as claimed in claim 1, and wherein:

ring A is piperidine ring, and may optionally be mono- or di-substituted by optionally substituted C1-6 alkyl or C1-6 alkoxy, each substituent being independently selected from halogen, C1-6 alkyl or an oxo group;

R3 is hydrogen, halogen, NO$_2$, CF$_3$, C1-4 alkyl, and C1-4 alkoxy, n is 1 or 2;

ring B is monocyclic or bicyclic heteroaryl having up to 10 ring atoms;

P is —O—, —CO—N(R6), or —(CH$_2$)$_n$— wherein n is 0 or 1;

R1 is hydrogen, C1-6 alkyl, C5-7 cycloalkyl, up to C12 aralkyl, up to C11 heteroarylalkyl, up to C10 aryl or C10 heteroaryl; all optionally substituted by up to three halogen atoms, or by CF$_3$;

R2 is hydrogen, or together with R1 represents a carbocyclic or heterocyclic spiro 5- or 6- membered ring;

R4 is up to C10 aryl optionally substituted by halogen, NO$_2$, CN, CF$_3$, C1-6 alkyl, —S—C1-6 alkyl, —SO—C1-6 alkyl, —S$_2$—C1-6 alkyl or C1-6 alkoxy;

or a pharmaceutically acceptable salt or in vivo hydrolysable precursor thereof.

3. A compound of claim 1, wherein ring B substituted by R3$_n$ is 5-chloro-2-pyridyl; P is a direct bond; ring A is piperidinyl; Y is SO$_2$, Q is —CH$_2$—, and Z is —N(OH)CHO; or a pharmaceutically acceptable salt or in vivo hydrolysable precursor thereof.

4. A compound of claim 1, wherein ring B is 5-chloro-2-pyridyl; P is a direct bond; Y is SO$_2$, Q is —CH$_2$—, Z is —N(OH)CHO and R1 is phenyl, phenbutylene, phenisopropylene, 2-pyridylethylene, phenisopropylene, 3-pyridylisopropylene, 4-pyridylisopropylene, or 4-chlorophenyloxydimethylmethylene; or a pharmaceutically acceptable salt or in vivo hydrolysable precursor thereof.

5. A pharmaceutical composition which comprises a compound of claim 1 or a pharmaceutically acceptable salt or an in vivo hydrolysable ester thereof.

6. A process for preparing a compound of formula (I) according to claim 1 or a pharmaceutically acceptable salt or in vivo hydrolysable ester thereof which process comprises a) reacting a compound of the formula (II) or a pharmaceutically acceptable salt or in vivo hydrolysable ester thereof with a compound of the formula (III)

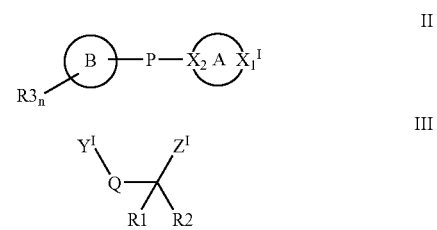

wherein $X_1^I$ represents X or a precursor of X (whether by modification or displacement) or an activated form of X suitable for reaction with $Y^I$;

$Y^I$ represents Y, a precursor of Y, or an activated form of Y suitable for reaction with $X_1^I$; $Z^I$ represents a protected form of Z, a precursor of Z (whether by modification or displacement of $Z^I$) or an activated form of Z;

and where Q is —(CH$_2$)(R6)— then by reacting a compound of the formula (IX) with an appropriate compound of the formula R1—CO—R2 to yield an alkene of the formula (X), which is then converted to a compound of the formula (XI) wherein Z* is a hydroxylamine precursor of the group Z, and then converting Z* to the group Z, all as set out below:

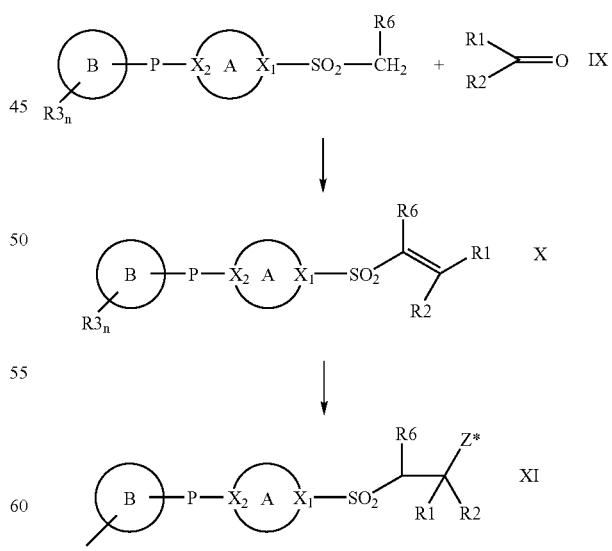

or b) reacting a compound of the formula (IV) or a pharmaceutically acceptable salt or in vivo hydrolysable ester thereof with a compound of the formula (V):

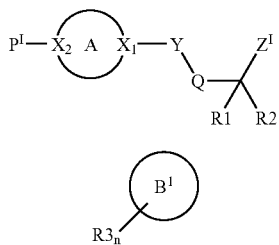

wherein $B^I$ represents a suitable ring function or substituent group for reaction with $P^I$;

$Z^I$ is as hereinbefore defined; and $P^I$ represents a suitably activated form of the linker P for reaction with $B^1$ or where $X_2$ is N then $P^I$ may be present on ring A rather than ring B or, as required, the linker P may be formed by appropriate reaction of precursor groups P'' and P''' provided on rings $B^1$ and A respectively, or vice versa.

7. A compound of claim 1, wherein a ring substituent on ring A is an oxo group that is adjacent to a ring nitrogen atom.

* * * * *